US012588903B2

(12) United States Patent
Bass et al.

(10) Patent No.: US 12,588,903 B2
(45) Date of Patent: Mar. 31, 2026

(54) ANTERIOR TO THE PSOAS SURGICAL ACCESS SYSTEM AND A MODIFIED SURGICAL APPROACH TECHNIQUE

(71) Applicant: TEDAN SURGICAL INNOVATIONS, INC., Sugarland, TX (US)

(72) Inventors: Daniel Bass, Sugarland, TX (US); Kaitlin Hom, Sugarland, TX (US); Eduardo Asturias, Sugarland, TX (US); Robert Mastny, Sugarland, TX (US); Thomas Terramani, Sugarland, TX (US)

(73) Assignee: TEDAN SURGICAL INNOVATIONS, INC., Sugarland, TX (US)

( * ) Notice: Subject to any disclaimer, the term of this patent is extended or adjusted under 35 U.S.C. 154(b) by 359 days.

(21) Appl. No.: 18/042,130

(22) PCT Filed: Jul. 29, 2021

(86) PCT No.: PCT/US2021/043754
§ 371 (c)(1),
(2) Date: Feb. 17, 2023

(87) PCT Pub. No.: WO2022/026746
PCT Pub. Date: Feb. 3, 2022

(65) Prior Publication Data
US 2023/0309982 A1    Oct. 5, 2023

Related U.S. Application Data

(60) Provisional application No. 63/104,398, filed on Oct. 22, 2020.

(51) Int. Cl.
| | |
|---|---|
| *A61B 17/02* | (2006.01) |
| *A61B 17/70* | (2006.01) |
| *A61B 90/30* | (2016.01) |

(52) U.S. Cl.
CPC ...... *A61B 17/0293* (2013.01); *A61B 17/7079* (2013.01); *A61B 90/30* (2016.02)

(58) Field of Classification Search
None
See application file for complete search history.

(56) References Cited

U.S. PATENT DOCUMENTS

| | | | |
|---|---|---|---|
| 8,137,284 B2 | 3/2012 | Miles | |
| 8,974,381 B1 * | 3/2015 | Lovell | A61B 90/30 600/222 |

(Continued)

FOREIGN PATENT DOCUMENTS

| | | | | |
|---|---|---|---|---|
| WO | WO-2015054070 A1 * | 4/2015 | ......... | A61B 17/7055 |
| WO | 2016/160397 A1 | 10/2016 | | |

OTHER PUBLICATIONS

Tedan Surgical Innovations, "Phantom AL Anterior Lumbar Access System," 2019, pp. 1-16, www.tedansurgical.com.

(Continued)

*Primary Examiner* — Julianna N Harvey
*Assistant Examiner* — Anna V. Little
(74) *Attorney, Agent, or Firm* — Kramer & Amado, P.C.

(57) ABSTRACT

An supine anterior-to-psoas approach includes a patient being rotated for the initial approach. Further, various blades and retractor rings provide various features to allow for the supine ATP approach or a conventional ATP to be performed.

21 Claims, 20 Drawing Sheets

500

(56) References Cited

U.S. PATENT DOCUMENTS

| 10,406,054 | B1 * | 9/2019 | Scholl | A61G 13/06 |
| 2002/0111538 | A1 | 8/2002 | Wright | |
| 2003/0004401 | A1 | 1/2003 | Ball | |
| 2005/0065410 | A1 | 3/2005 | Bjork | |
| 2005/0080319 | A1 | 4/2005 | Dinkler | |
| 2007/0179614 | A1 * | 8/2007 | Heinz | A61F 2/4611 |
| | | | | 623/17.14 |
| 2008/0058606 | A1 * | 3/2008 | Miles | A61B 1/32 |
| | | | | 600/214 |
| 2015/0265265 | A1 * | 9/2015 | Hynes | A61B 90/30 |
| | | | | 600/219 |
| 2016/0287234 | A1 | 10/2016 | Bass | |
| 2017/0333023 | A1 * | 11/2017 | Adams | A61B 17/0293 |
| 2018/0168566 | A1 * | 6/2018 | O'Connell | A61B 90/57 |
| 2018/0206834 | A1 * | 7/2018 | Villamil | A61B 17/0218 |
| 2019/0083283 | A1 * | 3/2019 | Sharifi-Mehr | A61F 2/4455 |

OTHER PUBLICATIONS

European Search Report mailed on Jul. 1, 2024 for corresponding European Patent Application No. 21850965.
International Search Report and Written Opinion for PCT/US2021/043751 mailed on Dec. 30, 2021.

* cited by examiner

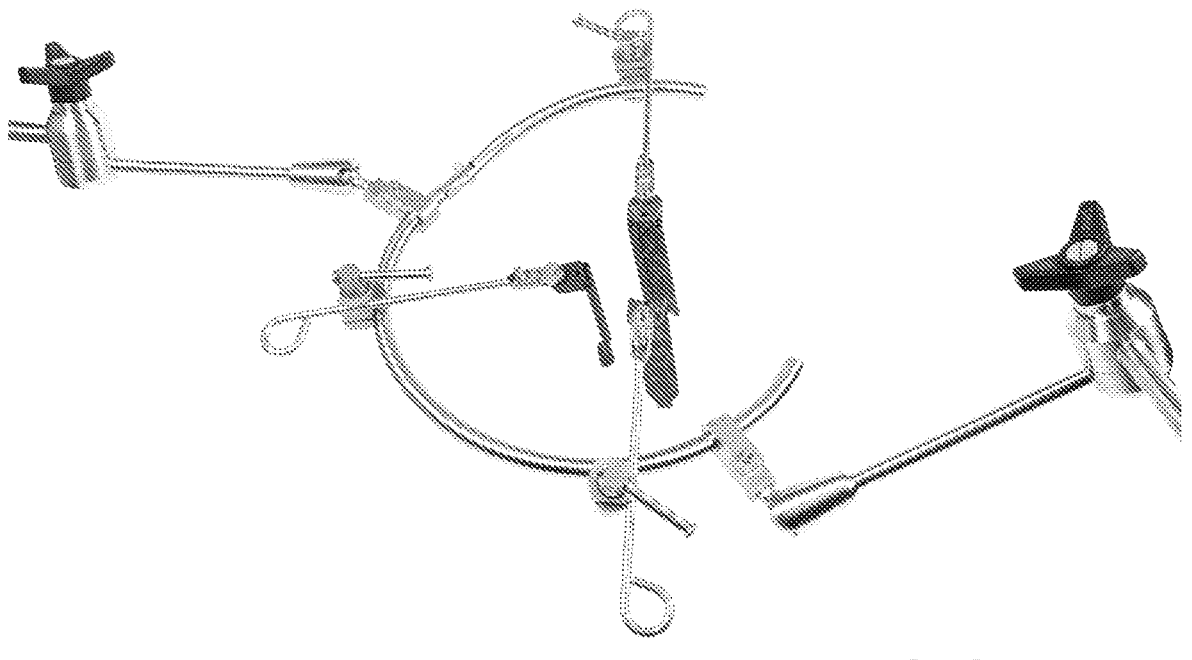
FIG. 3A
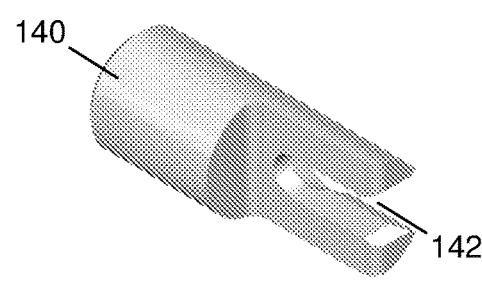
FIG. 4A
FIG. 4B

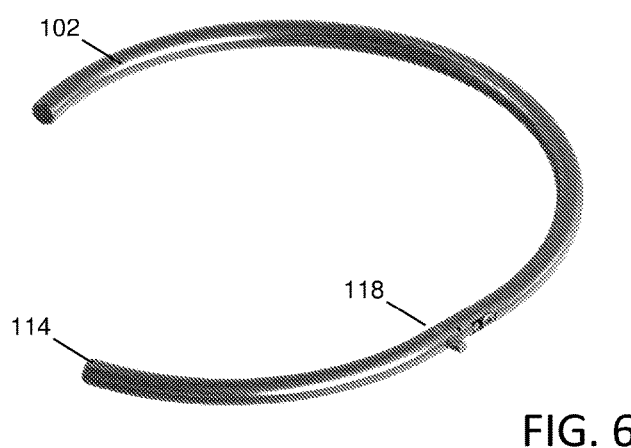
FIG. 6
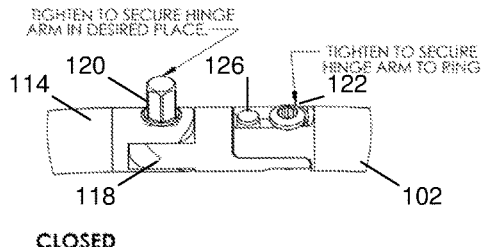
TIGHTEN TO SECURE HINGE
ARM IN DESIRED PLACE.
TIGHTEN TO SECURE
HINGE ARM TO RING.
CLOSED
FIG. 3D
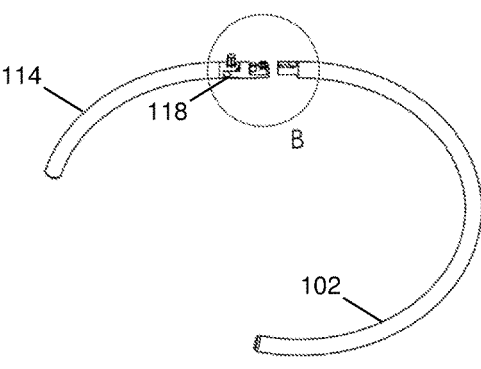
LOOSEN TO ROTATE
HINGE ARM.
LOOSEN SCREW WITH HEX
DRIVER TO REMOVE FROM RING.
SEPARATE AFTER
LOOSENING SCREW
OPEN
FIG. 3E
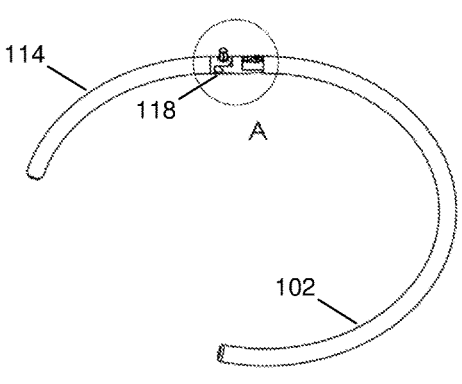
A
FIG. 3B
B
FIG. 3C

500

108

112

104

106

112

502

110

502

504

506

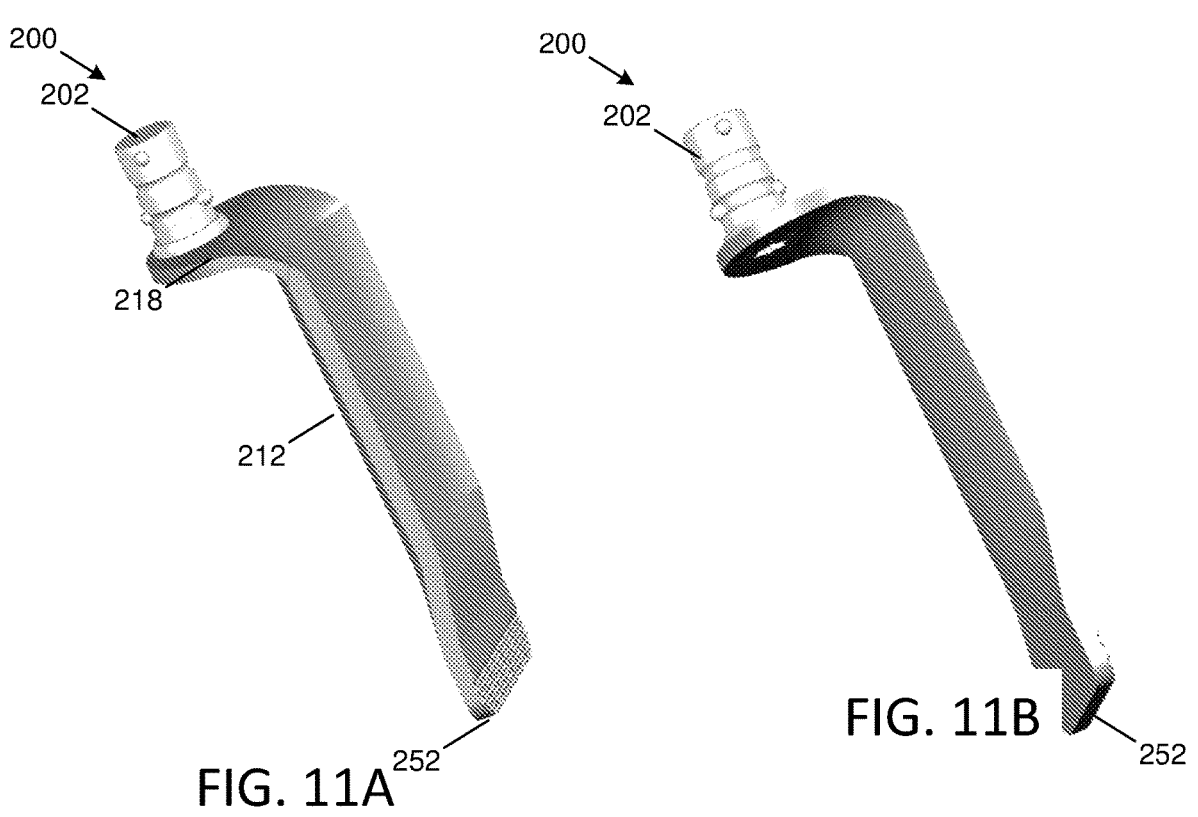
FIG. 11A
FIG. 11B
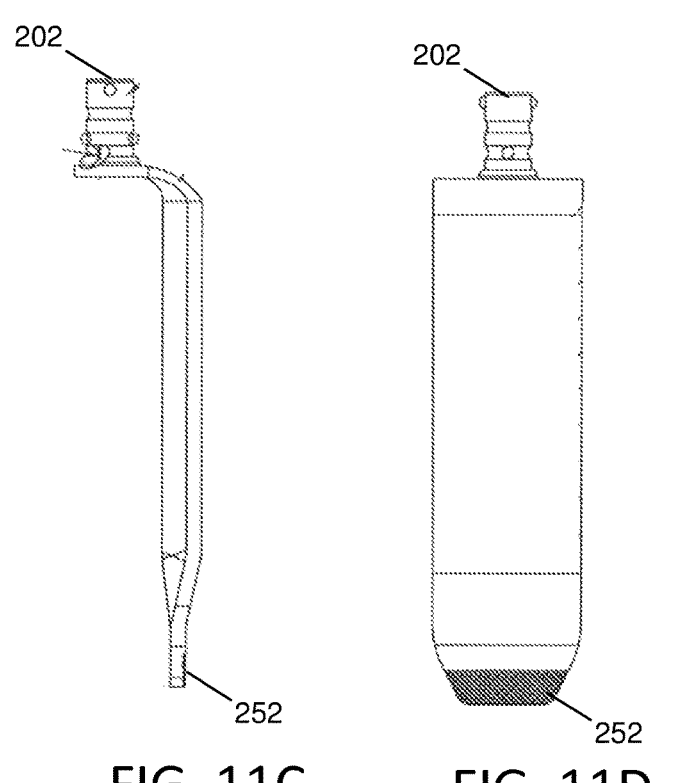
FIG. 11C    FIG. 11D    FIG. 11E

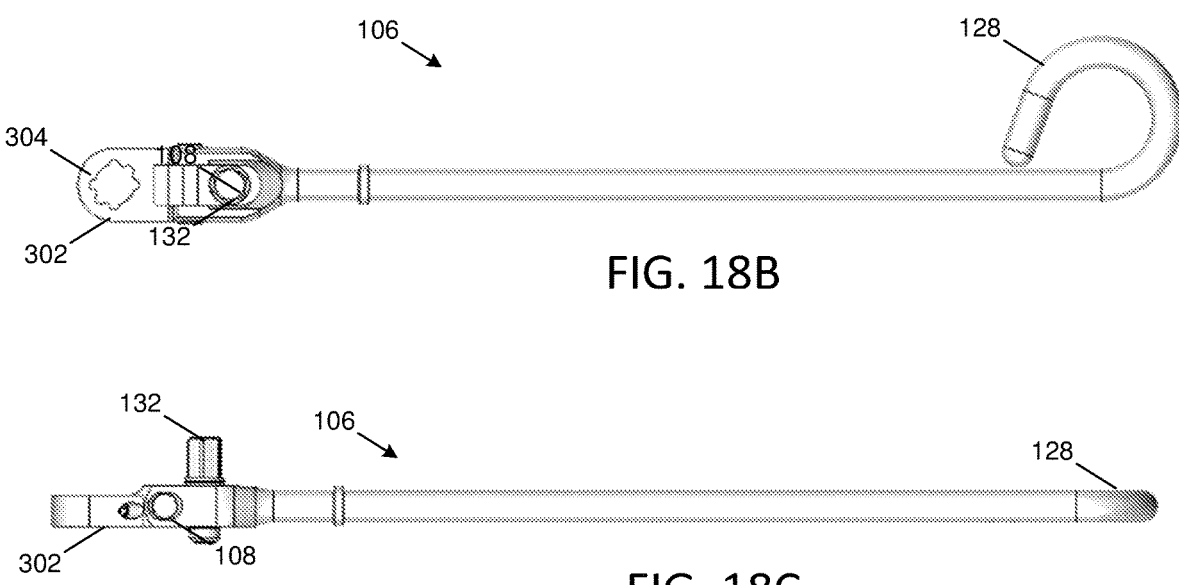
FIG. 18B
FIG. 18C
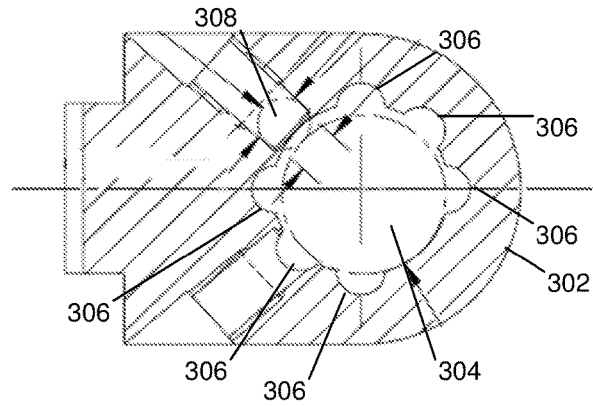
FIG. 19

ANTERIOR TO THE PSOAS SURGICAL ACCESS SYSTEM AND A MODIFIED SURGICAL APPROACH TECHNIQUE

CROSS-REFERENCE TO RELATED APPLICATIONS

This application claims benefit to U.S. Provisional Patent Application Nos. 63/104,398 filed on Oct. 22, 2020, and 63/059,160 filed on Jul. 30, 2020, the contents of each which are hereby incorporated by reference for all purposes as if fully set forth herein.

TECHNICAL FIELD

Various exemplary embodiments disclosed herein relate generally to an anterior to the psoas (ATP) surgical access system.

BACKGROUND

Various methods and approaches have been used to perform spinal surgery. These various methods approach the spine from different directions. In order to facilitate spinal surgery and to provide access to the spine various devices and systems including retractors are used to provide a surgical corridor for a surgeon to perform the needed surgical procedure.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a hinged retractor ring, including: a first ring portion; a second ring portion; and a first hinge connecting the first ring portion, wherein the first hinge allows the first ring portion and the second ring portion to be fixed at a neutral or variable angle to one another, and wherein the first ring portion and the second ring portion form the retractor ring.

Various embodiments are described, wherein the first hinge allows for a removable connection between the first ring portion and the second ring portion.

Various embodiments are described, further including; a third ring portion; and a second hinge connecting the third ring portion to the first ring portion.

Various embodiments are described, further including; a second hinge connecting the first ring portion to the second ring portion, wherein the first ring portion and the second ring portion are half of the retractor ring.

Various embodiments are described, wherein the first hinge and the second hinge are configured to be connected between the first and second ring portions and to be removed from between the first and second ring portions.

Various embodiments are described, further including a cap configured to attach to an end of the first ring portion.

Various embodiments are described, wherein the first ring portion and the second ring portion create a partial hinged retractor ring.

Various embodiments are described, wherein the hinged retractor ring is made of a semi-radio-lucent or radio-lucent material.

Various embodiments are described, wherein the hinged retractor ring plated with a metal to enhance mechanical and wear capability without interfering with radio-lucent properties of the base material.

Further various embodiments relate to a method for preparing a retractor ring for a surgical procedure, including: separating a first half of the retractor ring from a second half of the retractor ring; connecting a first hinge between the first half of the retractor ring and the second half of the retractor ring; positioning the first half of the retractor ring at an angle relative to the second half of the retractor ring; and securing the position of the hinge to fix the position of the first half of the retractor ring relative to the second half of the retractor ring.

Further various embodiments relate to a method for preparing a retractor ring for a surgical procedure, including: selecting a first ring portion; selecting a second ring portion; connecting a first hinge between the first ring portion and the second ring portion; positioning the first ring portion at an angle relative to the second ring portion; and securing the position of the hinge to fix the position of the first ring portion relative to the second ring portion, wherein the combination of the first ring portion and the second ring portion form a partial ring.

Further various embodiments relate to a retractor blade, including: a base; a body extending at an angle from the base wherein the body includes: a fixation channel at an edge of the body; and a utility channel along the body configured to accept a sliding element; a stem extending from the base in a direction opposite for the body wherein the stem includes: a first circular groove; a second circular groove; a first cross-pin; and a second cross-pin; and a channel extending from a first opening in the base to an interior opening on the body.

Various embodiments are described, wherein the body includes a curved tip that curves inward towards a surgical site away from the stem.

Various embodiments are described, wherein the body includes a curved tip that curves outward away from a surgical site towards the stem.

Various embodiments are described, wherein the channel is configured to guide a device towards interior opening of the body.

Various embodiments are described, wherein the device includes one of a camera, suction, and a light source.

Various embodiments are described, wherein the sliding element is configured to fix the sliding element to the utility channel.

Further various embodiments relate to a retractor blade, including: a base; a body extending at an angle from the base wherein the body includes a utility channel along the body configured to accept a sliding element; a stem extending from the base in a direction opposite for the body wherein the stem includes: a first circular groove; a second circular groove; a first cross-pin; and a second cross-pin; and a channel extending from a first opening in the base to an interior opening on the body, wherein the body includes a curved tip that curves inward towards a surgical site away from the stem.

Various embodiments are described, wherein the channel is configured to guide a device towards interior opening of the body.

Various embodiments are described, wherein the device includes one of a camera, suction, and a light source.

Various embodiments are described, wherein the sliding element is configured to fix the sliding element to the utility channel.

Further various embodiments relate to a method for surgically approaching the spine of a patient for spinal surgery, including: positioning the patient on an operating table in supine position in an approximately horizontal orientation; rotating the patient about a superior-inferior axis of the patient, so that the patients left side is higher than the patients right side; performing an anterior-to-psoas (ATP) surgical approach to the spine; placing one or more retractors to create a surgical corridor to the spine; affixing the one or more retractors to a retractor frame; rotating the patient back to the approximately horizontal position; and performing a surgical procedure though the surgical corridor.

Various embodiments are described, including securing the patient to operating table, wherein rotating the patient includes rotating the operating table.

Various embodiments are described, including deploying one or more positioners on the right side of the patient.

Various embodiments are described, including deploying a first positioner under the right arm of the patient and a second positioner just above the right knee.

Various embodiments are described, including determining the location of the incision using imaging to identify the appropriate in-line trajectory to a targeted lumbar disc space.

Various embodiments are described, including marking the abdominal wall at the anterior axillary line based upon the identified in-line trajectory.

Various embodiments are described, including configuring a retractor frame which is a supine ATP ring with a first hinge arranged at a cranial position and the second hinge arranged a second caudal position, wherein the hinges are angled at approximately 20 degrees to 30 degrees.

Various embodiments are described, wherein one of the retractor blades is a flat end blade that is positioned by levering against the anterior aspect of the lumbar spine retracting the intraabdominal package and maintaining the retroperitoneal space.

Various embodiments are described, wherein the flat end blade is connected to the supine ATP ring at position between the hinges on the left side of the patient.

Various embodiments are described, wherein the patient is rotated approximately 20 degrees to 30 degrees left side up.

Various embodiments are described, wherein one of the retractor blades is second blade that is placed an approximal cranial position on the supine ATP ring and one of the retractor blades is third blade that is placed an approximal caudal position on the supine ATP ring.

Various embodiments are described, further including securing the second blade and the third blade to a vertebral body.

Various embodiments are described, wherein one of the retractor blades is reverse tip blade that is placed to retract a left psoas muscle from the surgical corridor and attached at a position between the hinges on the right side of the patient.

Various embodiments are described, including performing a disc preparation on the left side of the patient.

Various embodiments are described, including implanting a device in the spine.

Various embodiments are described, including delivering the device to the spine using a sliding element in a channel of one of the retractor blades.

Various embodiments are described, including lighting the surgical corridor using a light source on a sliding element in a channel of one of the retractor blades.

Various embodiments are described, including applying suction to the surgical corridor using a suction device on a sliding element in a channel of one of the retractor blades.

Various embodiments are described, including lighting the surgical corridor using a light source in a channel of one of the retractor blades, wherein the channel extends from the top of a base of the retractor blade to a surface of the retractor blade facing the surgical corridor.

Various embodiments are described, including applying suction to the surgical corridor using a suction device in a channel of one of the retractor blades, wherein the channel extends from the top of a base of the retractor blade to a surface of the retractor blade facing the surgical corridor.

Various embodiments are described, including securing one of the retractor blades to vertebral body using a fastener inserted through a fastening channel extending along the length of the retractor blade.

Further various embodiments relate to a retractor blade assembly, including: an arm member; a retractor blade having stem member provided at a top of the blade, the stem member including a first pin member, provided at an upper portion of the stem member, having at least one abutment extending outward from the stem member, a first groove provided below the first pin member, provided about the circumference of the stem member, a second groove provided below the first groove, provided about the circumference of the stem member, a second pin member having at least one abutment extending from the second groove, a blade connector including a body including a first aperture and at least four pin slots, extending from a top surface of the body through a bottom surface of the body and configured to receive insertion of the stem member therein, the blade connector further including a second aperture extending from a side wall into an interior of the body in communication with the first aperture, and a locking assembly provided in the second aperture configured to selectively engage the first groove and the second groove of the stem member in an inserted position; wherein when the stem member of the retractor blade is inserted in the first aperture in a first position, the locking assembly engages the first groove of the stem member, the first pin member is located above the top surface of the blade connector and the second pin member is located below the bottom surface of the blade connector, permitting the stem member and connected retractor blade to rotate, wherein when the stem member of the retractor blade is in a second position, the locking assembly engages the second groove of the stem member preventing vertical movement of the stem member, and at least one of the abutments of the second pin member is located in at least one of the pin slots of the blade connector, thereby locking the blade member in a locked position.

BRIEF DESCRIPTION OF THE DRAWINGS

In order to better understand various exemplary embodiments, reference is made to the accompanying drawings, wherein:

FIG. 3A illustrates the hinged ring;

FIGS. 3B-3E illustrate the hinge structure of the hinged ring;

FIGS. 4A and 4B illustrated perspective views of a cap;

FIGS. 11A-E illustrate a two perspective, back, side and front views of a flat retractor blade;

FIGS. 17 and 18A-C illustrate various embodiments of arms;

FIG. 19 illustrates a close up view of the head; and

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Performing spinal surgery using the anterior to the psoas (ATP) approach involves a minimally-invasive access to the lumbar disc space via a corridor between the peritoneum and the psoas muscle. Given this defined surgical passage, performing surgery with an ATP approach, does not require removal of bone (laminectomy, facetectomy or stripping of the spinal or paraspinal musculature). In contrast to the lateral surgical approach to the lumbar column, the ATP surgical corridor does not transverse the psoas muscle, which requires navigating adjacent to the lumbar plexus and the associated intraoperative neuromonitoring to avoid nerve damage-minimizing lumbar plexus and psoas injury as dissection is performed anterior to the psoas. The existing ATP approach is also suitable for wider range of disc levels, from L2 to S1 and allows for good disc access and preparation.

Figure 1A:
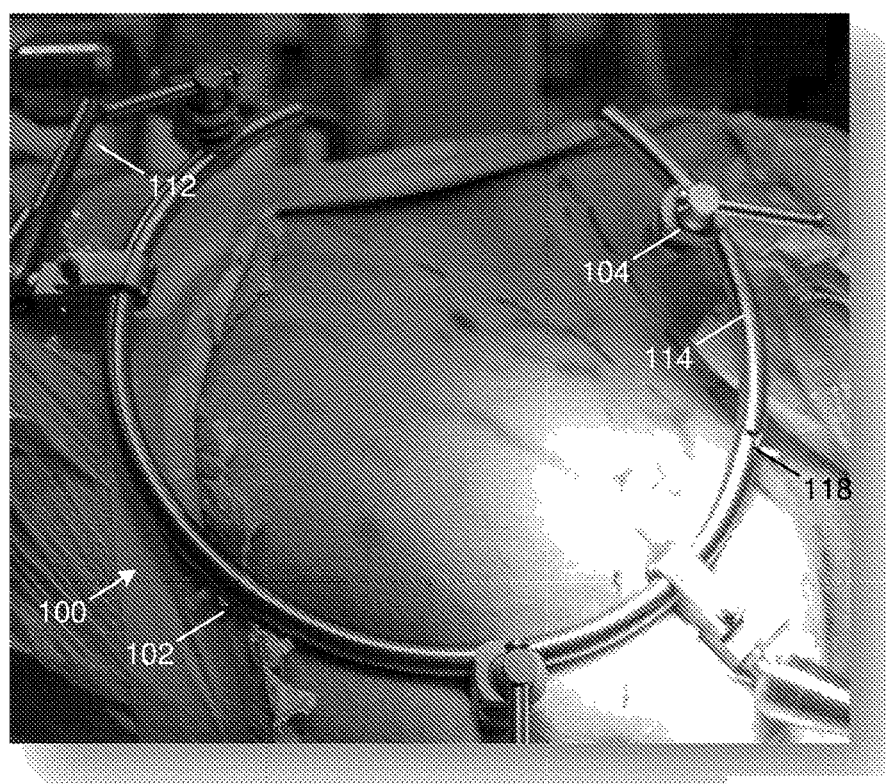
FIGS. 1A-1D illustrate various views of an ATP access system for the existing ATP approach to the lumbar spine column in various configurations.
Figure 1B:
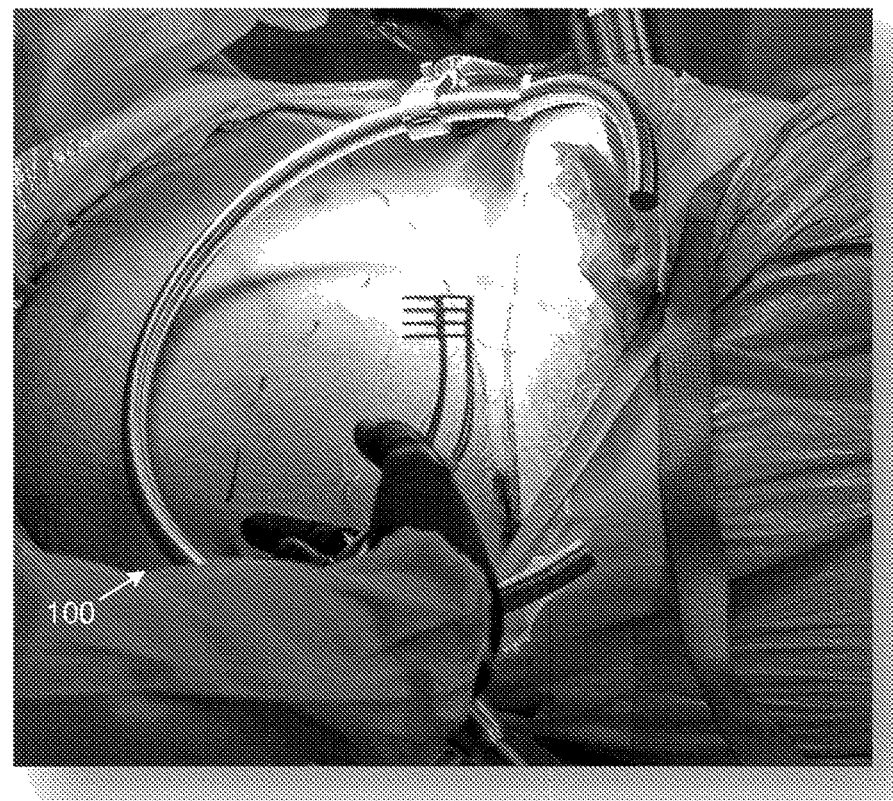
Figure 1C:
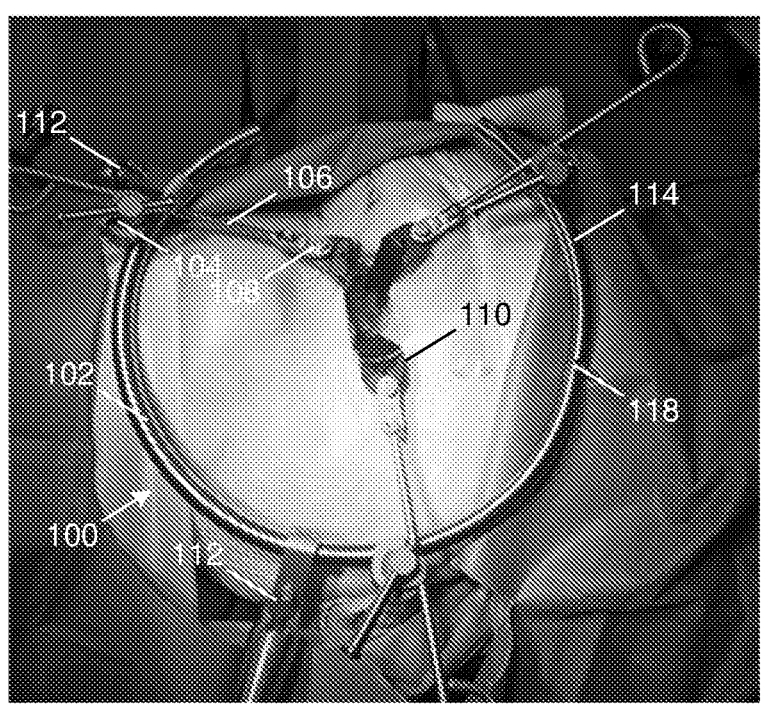
Figure 1D:
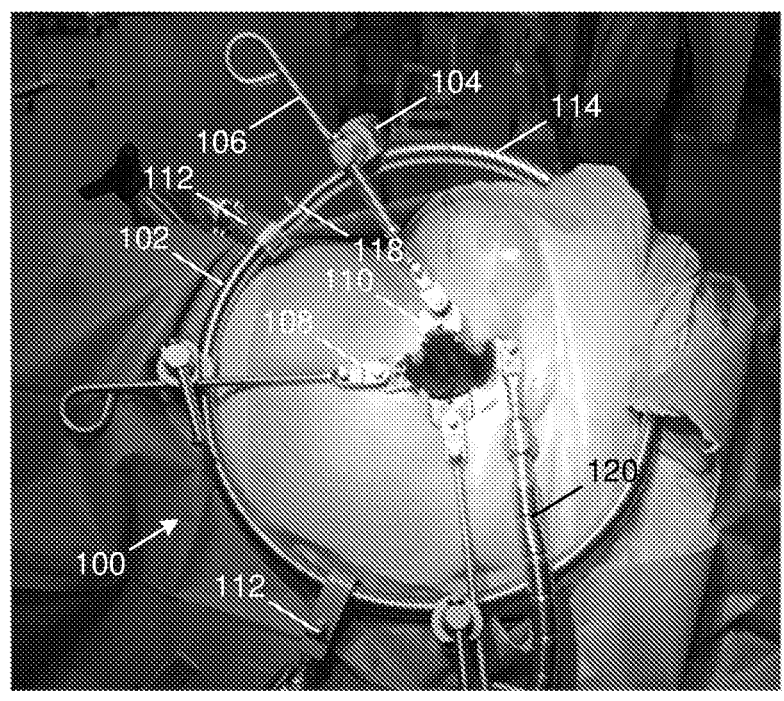
Figure 2A:
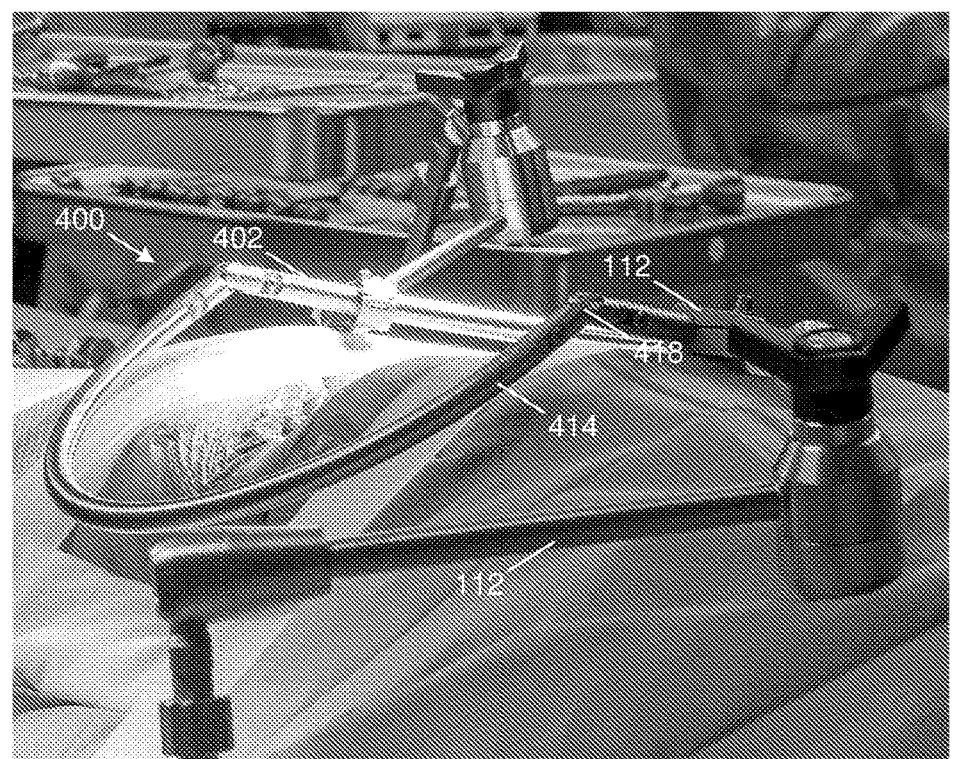
FIGS. 2A-2D illustrate a view of a configuration of a Supine ATP system for a Supine ATP approach for accessing the spine including a full ring configuration with hinged elements designed to cradle anterior-lateral aspect of the patient's anatomy.
Figure 2B:
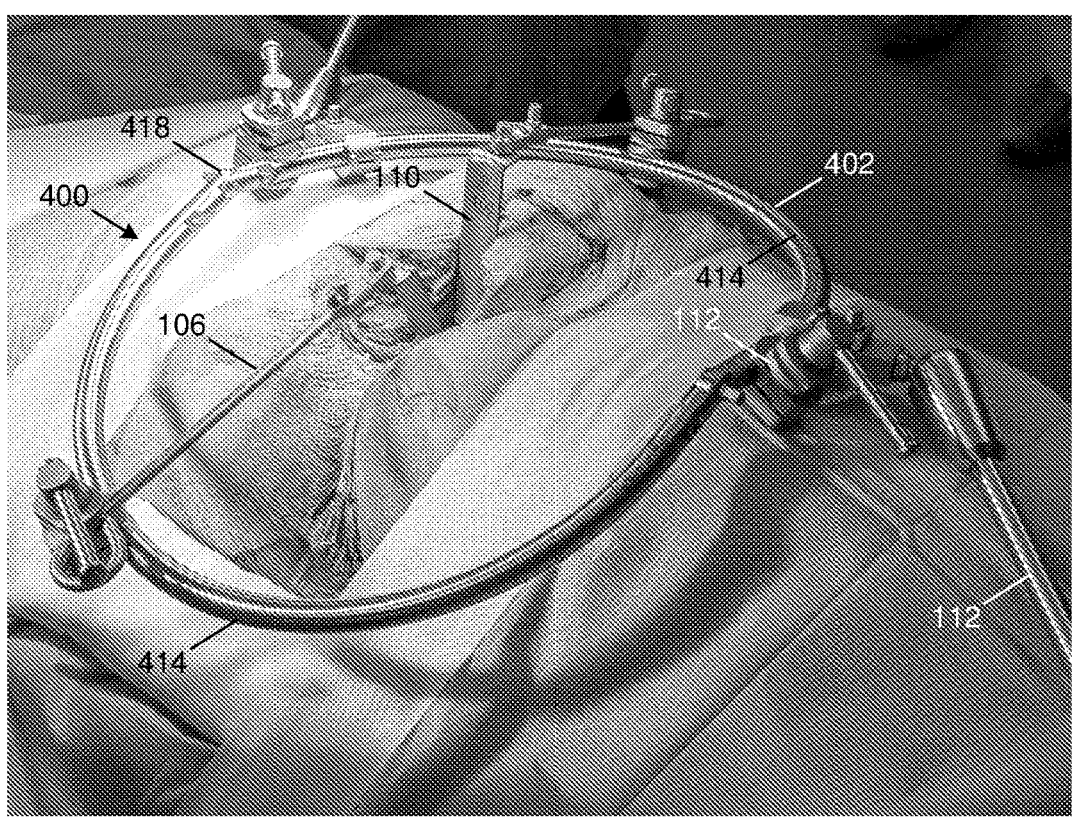
Figure 2C:
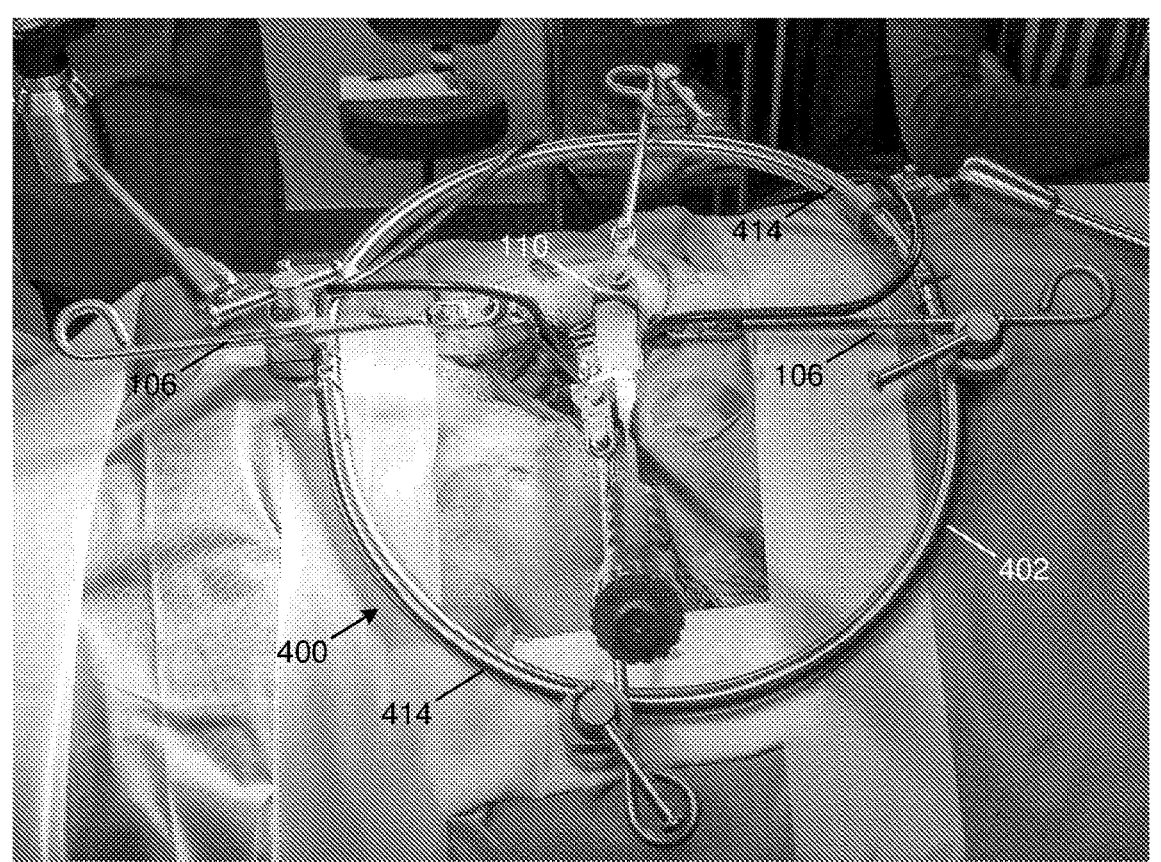
Figure 2D:
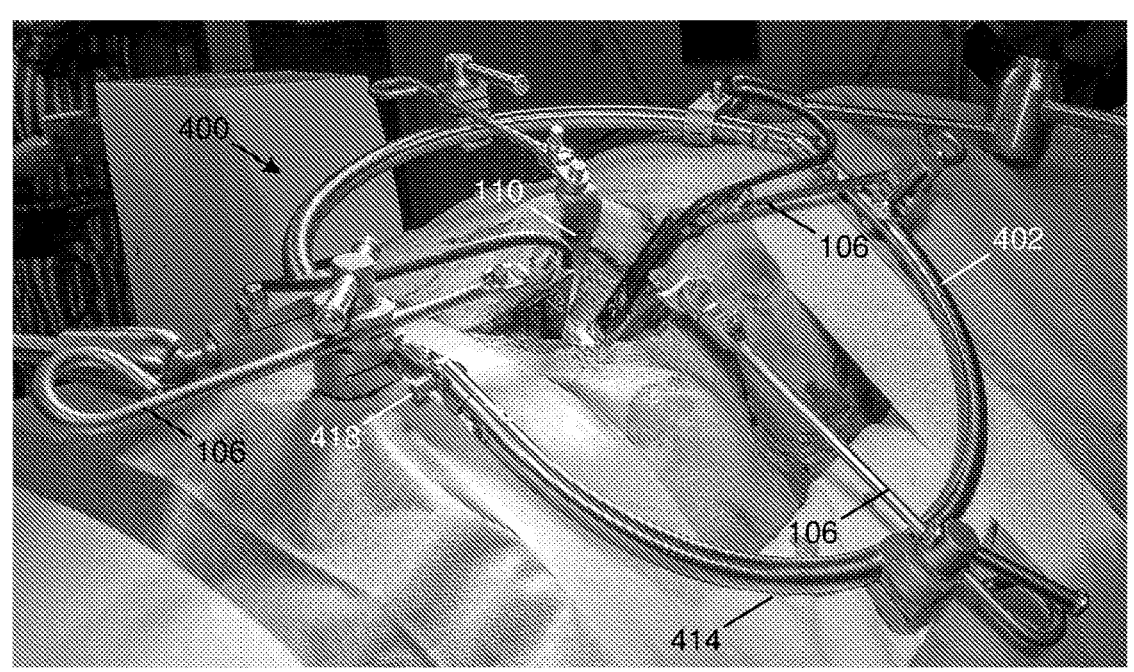

FIGS. 1A-1D illustrate various views of an ATP access system for the existing ATP approach to the lumbar spine column in various configurations. The ATP access system 100 facilitates a minimally invasive access to the lumbar spine from an oblique angle. FIGS. 1B,1D illustrate a configuration for accessing the L5/S1 levels of the lumbar spine with a hinged articulating ring enabling anatomical accommodation of the anterior aspect of the iliac spine when patient position is lateral to the operating room table. Various rigid arms 106 hold retractor blades 110 that form the surgical corridor. Also, an flexible accessory arm 120 can be optionally deployed to position a caudal fourth retractor blade to minimize intrusion of tissue into the operative site.

The ATP access system illustrated in FIGS. 1A-1D includes a ring 102, a clamp 104, an arm 106, an arm connector 108, a retractor blade 110, a ring support 112, a hinged ring extension 114, and a hinge 118. The ring 102 may be a partial ring that is half or three quarters of a circle, or any other portion of a circle. In other embodiments, the ring may be a complete circle. The ring 102 has a hinge 118 that connects a main portion of the ring 102 to the hinged ring extension 114. The main portion of the ring 102 may be a quarter, half, or any other portion of a full ring. The hinged ring extension 114 may be quarter of a full ring, or any other portion of a full ring. The ring hinge 118 allows the hinged ring extension 114 to be rotated out of the plane of the ring 102. This hinged configuration is illustrated in FIGS. 1A-1D where the hinged ring extension 114 is rotated from the ring 102 avoiding patient anatomy. The ability to adjust the location of the hinged ring extension 114 allows for better positioning of the ring 102 to avoid various anatomy of the patient in various access locations as well as the positioning of the retractor blades 110 around the surgical opening.

The ring 102 is held in place by ring supports 112. The ring support 112 includes a clamp that connects to the ring at one end of the ring support 112 and a ring support table clamp (not shown) at the opposite end of the ring support 112.

The clamps 104 are connected and fixed at different positions around the ring 102. The clamps 104 also connect to the arm 106. The arm 106 has an arm connector 108 at the distal end of the arm 106 from the clamp 104. The arm connector 108 connects to the blade 110. Typically, multiple arms 106 with attached blades 110 are used to retract tissue to maintain a surgical opening as illustrated in FIGS. 1A-1D.

A ring support 112 and table clamp attaches securely onto the operating table side rails. The other end of the ring support 112 has a clamp that securely attaches to the ring 102. The ring supports 112 may include straight, curved, or L-shaped articulating arms, which may be detachable for easy storage and handling. The ring supports 112 may include a number of different portions that are connected together using various articulating joints that allow for the ring to be placed in a precise location. Further, the ring supports 112 are heavy duty to prevent micro movement of the ATP access system 100.

FIGS. 2A-2D illustrate a view of a configuration of a Supine ATP system 400 for a Supine ATP approach for accessing the spine including a full ring configuration with hinged elements designed to cradle anterior-lateral aspect of the patient's anatomy. Due to its flexible configurative design, the Supine ATP access system 400 may be used as a universal system that may be used for three surgical approaches to the lumbar spine: lateral, anterior, and ATP either in a lateral decubitus, supine, or a Supine ATP approach, that is a modified oblique supine patient position. Various optional parts may be used to convert the Supine ATP access system 400 for use in the other approaches.

The Supine ATP access system 400 illustrated in FIGS. 2A-2D includes a ring 402, an arm 106, an arm connector 108, a retractor blade 110, a ring support 112, and a ring hinge 418. The ring 402 is a full ring. In other embodiments, the ring 402 may be a semicircular ring that is half or three quarters of a circle, or any other portion of a circle. The ring 402 has hinges 418 that connect hinged ring halves 402 to one another. The ring hinges 418 allow a hinged ring half 414 to be rotated out of the plane of the ring 402. This hinged configuration is illustrated in FIGS. 2A-2D where the hinged ring half 414 is rotated from the ring 402 avoiding patient anatomy. The ability to adjust the location of the hinged ring half 414 allows for better positioning of the ring 402 to avoid various anatomy of the patient in various access locations as well as the positioning of the retractor blades 110 around the surgical opening.

The ring 402 is held in place by ring supports 112. The ring support 112 includes a clamp that connects to the ring at one end of the ring support 112 and a ring support table clamp (not shown) at the opposite end of the ring support 112.

The clamps 104 are connected and fixed at different positions around the ring 402. The clamps 104 also connect to the arm 106. The arm 106 has an arm connector 108 at the distal end of the arm 106 from the clamp 104. The arm connector 108 connects to the blade 110. Typically, multiple arms 106 with attached blades 110 are used to retract tissue to maintain a surgical opening as illustrated in FIGS. 2A-2D.

A ring support 112 and table clamp attaches securely onto the operating table side rails. The other end of the ring support 112 has a clamp that securely attaches to the ring 402. The ring supports 112 may include straight, curved, or L-shaped articulating arms, which may be detachable for easy storage and handling. The ring supports 112 may include a number of different portions that are connected together using various articulating joints that allow for the ring to be placed in a precise location. Further, the ring supports 112 are heavy duty to prevent micro movement of the ATP access system 100.

FIG. 3A illustrates the hinged ring 102. The hinged ring extension 114 may be removable. FIGS. 3B-3E illustrate the hinge structure of the hinged ring 102. FIG. 3D illustrates a close up view of the ring hinge 118, with the hinged ring extension 114 connected to the hinged ring 102. FIG. 3B illustrates the hinged ring in a connected configuration corresponding the FIG. 3D. FIG. 3E illustrates a close up view of the ring hinge 118, with the hinged ring extension 114 separated from the hinged ring 102. FIG. 3C illustrates the hinged ring 102 in a separated configuration corresponding the FIG. 3E.

The hinged ring 102 includes an end with a hinge connection slot 124. The hinged ring extension 114 includes hinge screw 122 and hinge connector pin 126 that slides into the hinge connection slot 124 to align and secure the hinged ring extension 114 to the hinged ring 102. The hinge screw 122 may then be tightened to secure the hinged ring extension 114 to the hinged ring 102. The hinge connection slot 124 may have a frustoconical portion configured to accept the head of the hinge screw 122.

The hinge 118 may include a hinge bolt 120 that may be tightened to fix the hinge 118 in a specific configuration. Once the hinged ring extension 114 is in the desired position relative to the hinged ring 102, the hinge bolt 120 is tightened with an accessory tool. While a removable hinged ring extension 114 is illustrated, other embodiments may not include a removeable hinged ring extension 114. Further, in other embodiments two hinged ring extensions 114 may be attached to opposite ends of the hinged ring 102. In another embodiment, two hinged ring extensions 114 may be attached to one another and then attached to the hinged ring 102. In any of these further embodiments the hinged ring extensions may be removable or fixed to the hinged ring 102.

FIGS. 4A and 4B illustrated perspective views of a cap. The cap 140 includes a cap slot 142. The cap slot 142 engages an end of a ring. The cap slot 142 may have a shape similar to hinge connection slot 124. The cap 140 may be attached to an end of a ring to present a smooth end of the ring as opposed to the structures that are present to engage other elements of the system.

Figures 5, 6A:
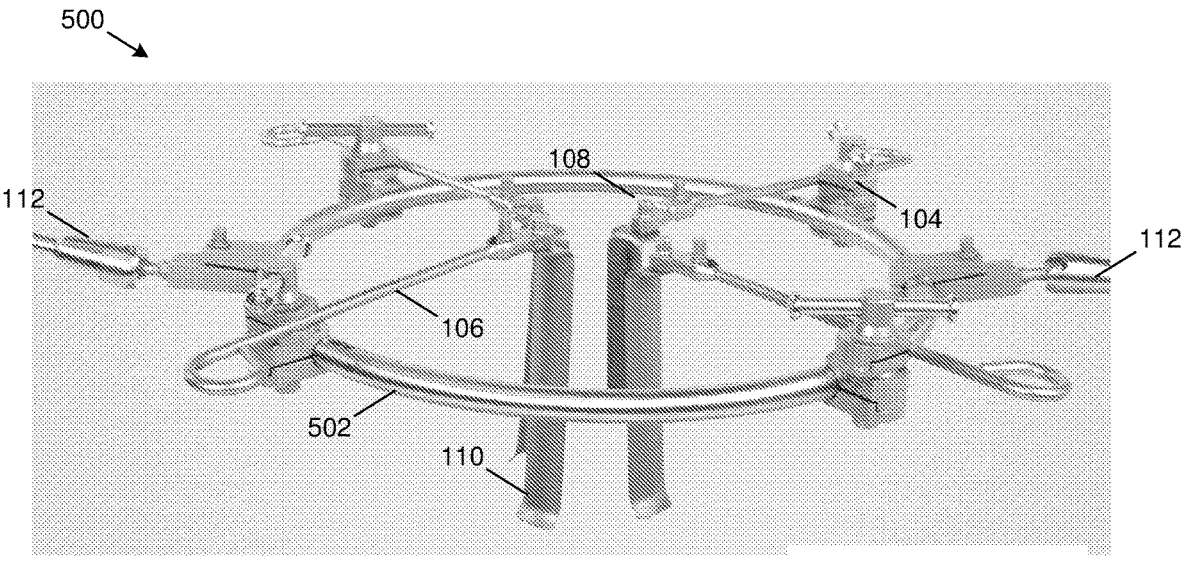
FIG. 5 illustrates a multi-approach ATP access system using modular ring.
FIG. 6A illustrates a perspective view of the modular ring.
Figures 6B, 6C, 7A, 7B, 7C:
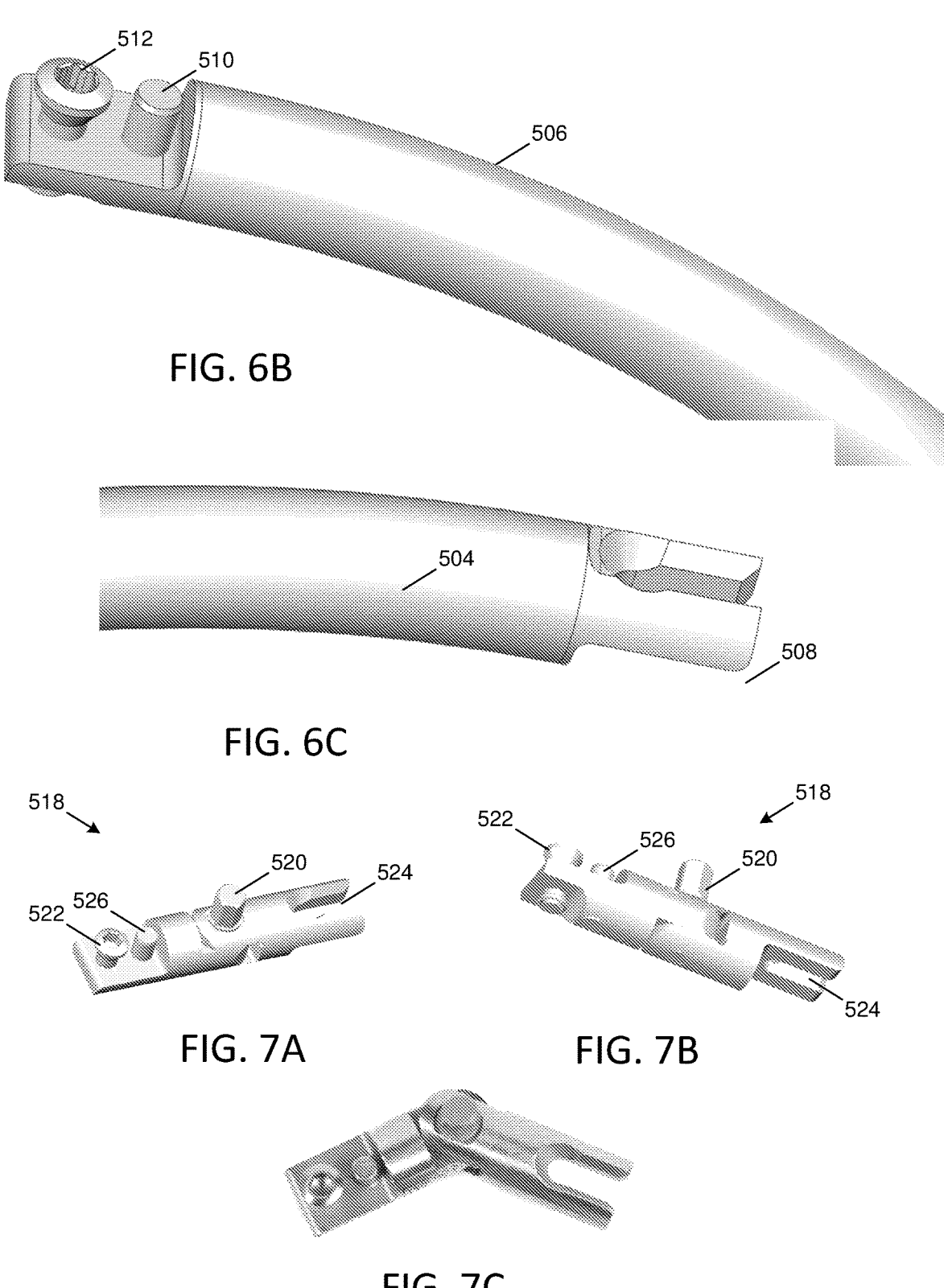
FIG. 6B illustrates an end of the first ring half.
FIG. 6C illustrates and end of the second ring half.
FIGS. 7A and 7B illustrated perspective views of hinges that may be used to convert the modular ring 502 to an articulating ring.
FIG. 7C shows the hinge in a bent position.

FIG. 5 illustrates a multi-approach ATP access system 500 using modular ring 502. It is shown with four clamps 104, four arms 106, and four blades 110. The modular ring 502 is illustrated in a flat configuration. FIG. 6A illustrates a perspective view of the modular ring 502. The modular ring 502 includes first ring half 504 and second ring half 506. FIG. 6B illustrates an end of the first ring half 504, and FIG. 6C illustrates and end of the second ring half 506. The end of the second ring half 506 includes a ring connector pin 510 and a ring screw 512. The end of the first ring half 504 includes a ring slot 508 configured to engage the ring connector pin 510 and the ring screw 512 . . . . The ring connector pin 510 slides into the ring slot 508 to align and secure the first ring half 504 to the second ring half 506. The ring screw 512 may then be tightened to secure the first ring half 504 to the second ring half 506. The ring slot 508 may have a frustoconical portion configured to accept the head of the ring screw 512.

The modular ring 502 may be adapted to be used in a Supine ATP approach with the addition of hinges. FIGS. 7A and 7B illustrated perspective views of hinges 518 that may be used to convert the modular ring 502 to an articulating ring. The hinge 518 includes a hinge connection slot 524. The hinge 518 also includes a hinge screw 522 and hinge connector pin 526 that slides into the ring slot 508 to align and secure the hinge 518 first ring half 504. The hinge screw 522 may then be tightened to secure the hinge 518 to the first ring half 504. The hinge connection slot 524 may have a frustoconical portion configured to accept the head of the ring screw 512. Likewise the ring connector pin may be slid into the hinge connection slot 524 to secure the hinge to the second ring half 506. FIG. 7C shows the hinge 518 in a bent position.

The hinge 518 may include a hinge bolt 520 that may be tightened to fix the hinge 518 in a specific configuration. Once the first ring half 504 in the desired position relative to the second ring half, the hinge bolt 520 is tightened with an accessory tool.

Figure 8:
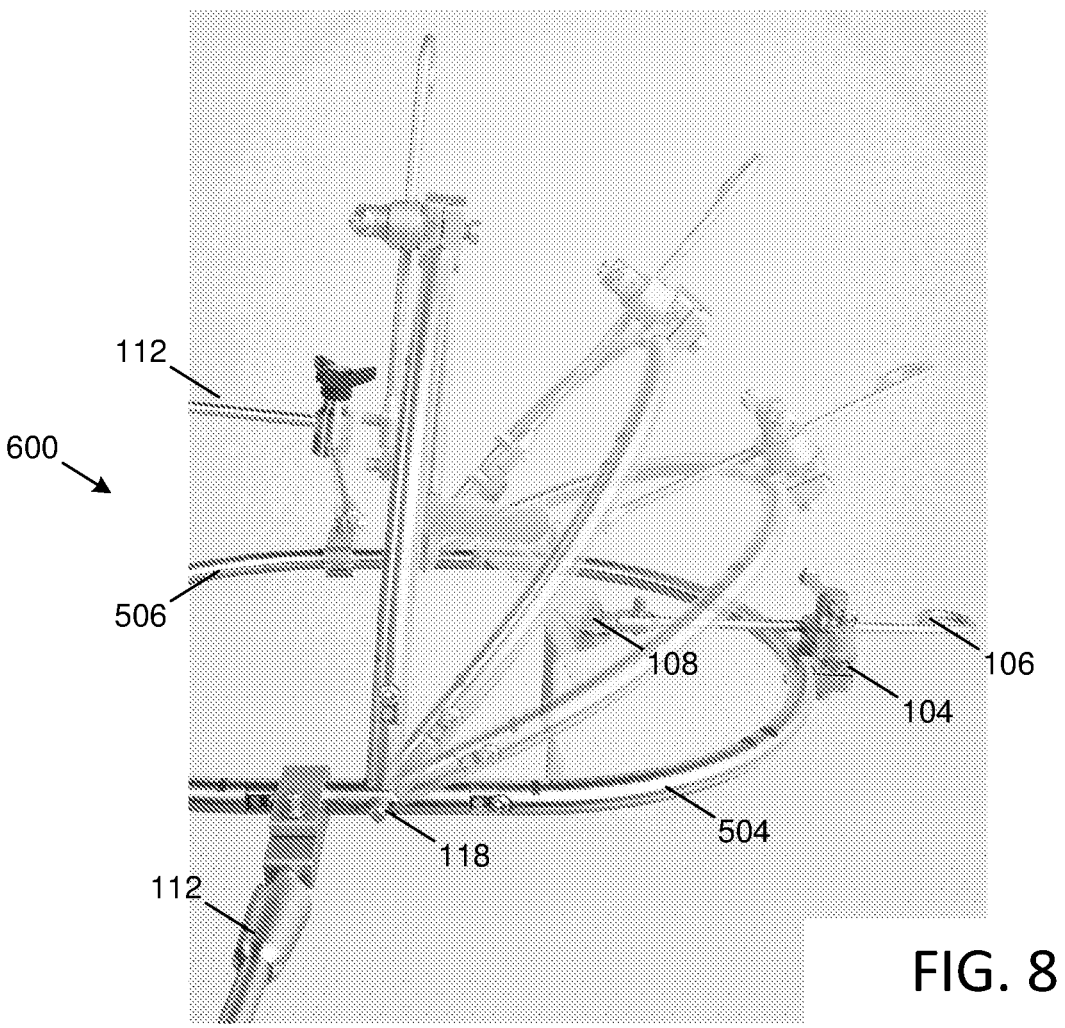
FIG. 8 illustrates an Supine ATP access system where the first ring half is shown in various angular positions relative to the second ring half.
Figures 9A, 9B, 9C, 9D, 9E:
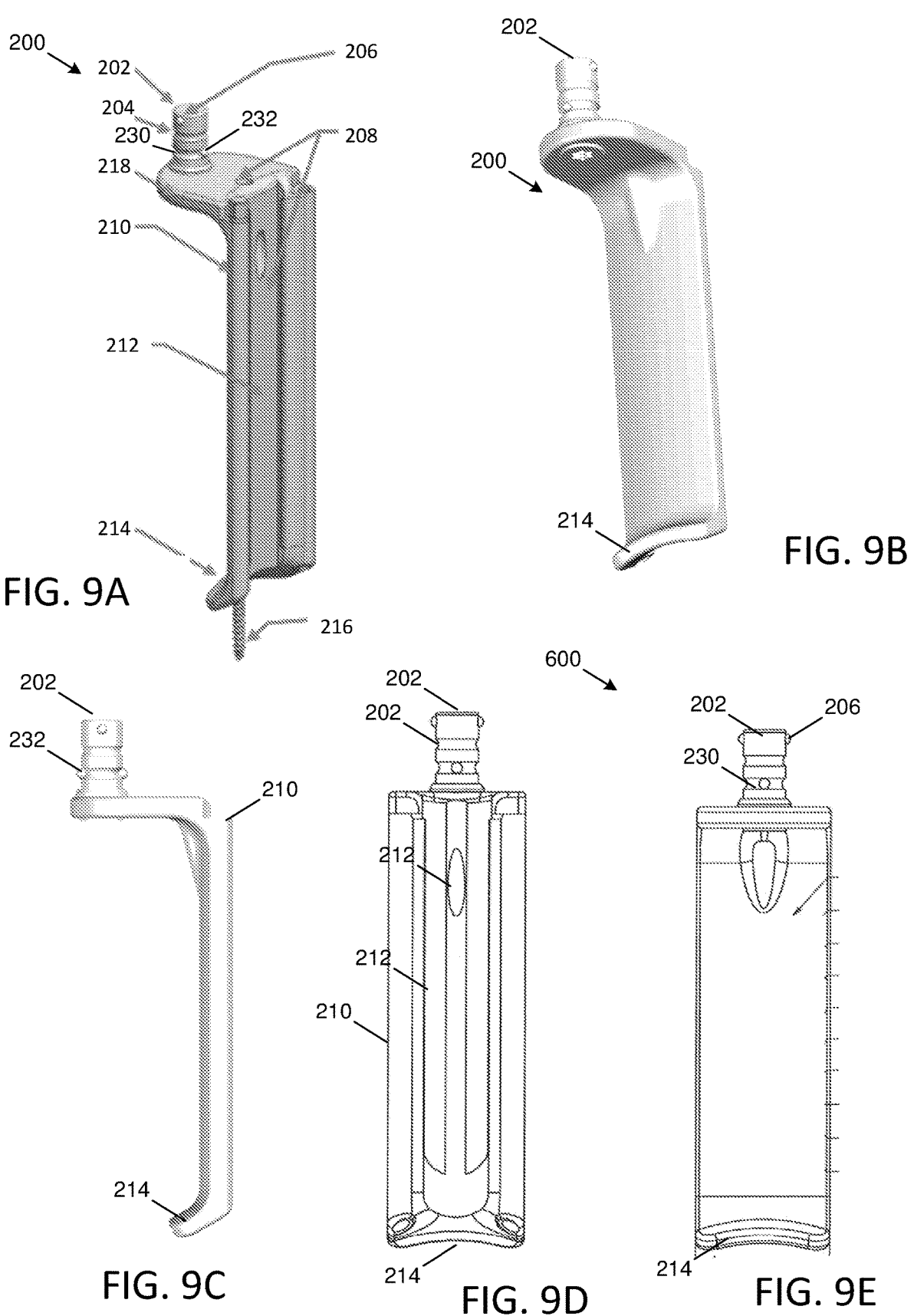
FIGS. 9A-9E illustrate two perspective views, as side view, a front view, and a back view, respectively, of a retractor blade with utility channel and cannulation.
Figures 10A, 10B, 10C, 10D, 10E:
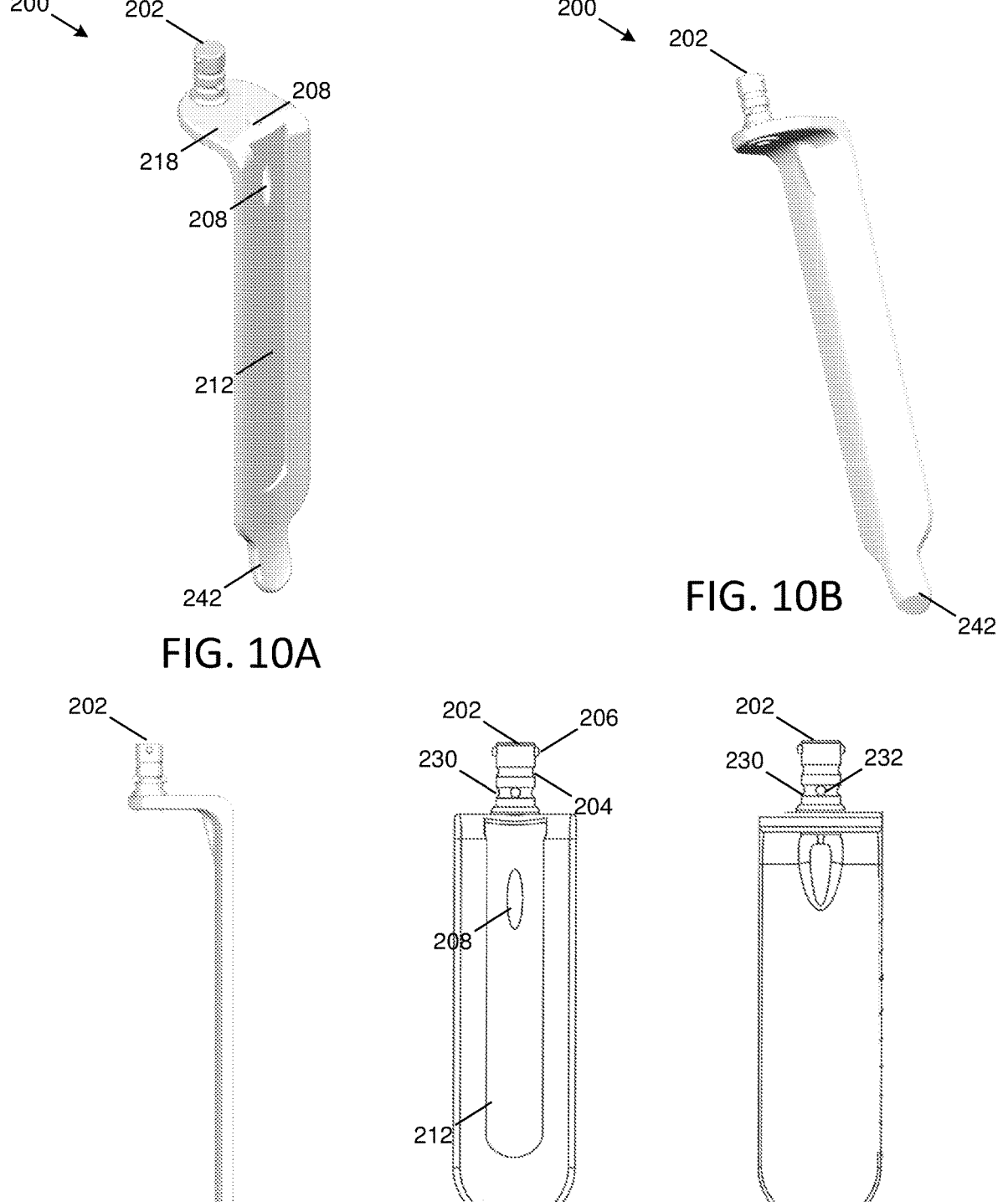
FIGS. 10A-E illustrate a two perspective, back, side and front views of a reverse tip blade retractor blade.
Figures 12A, 12B, 12C, 12D, 12E:
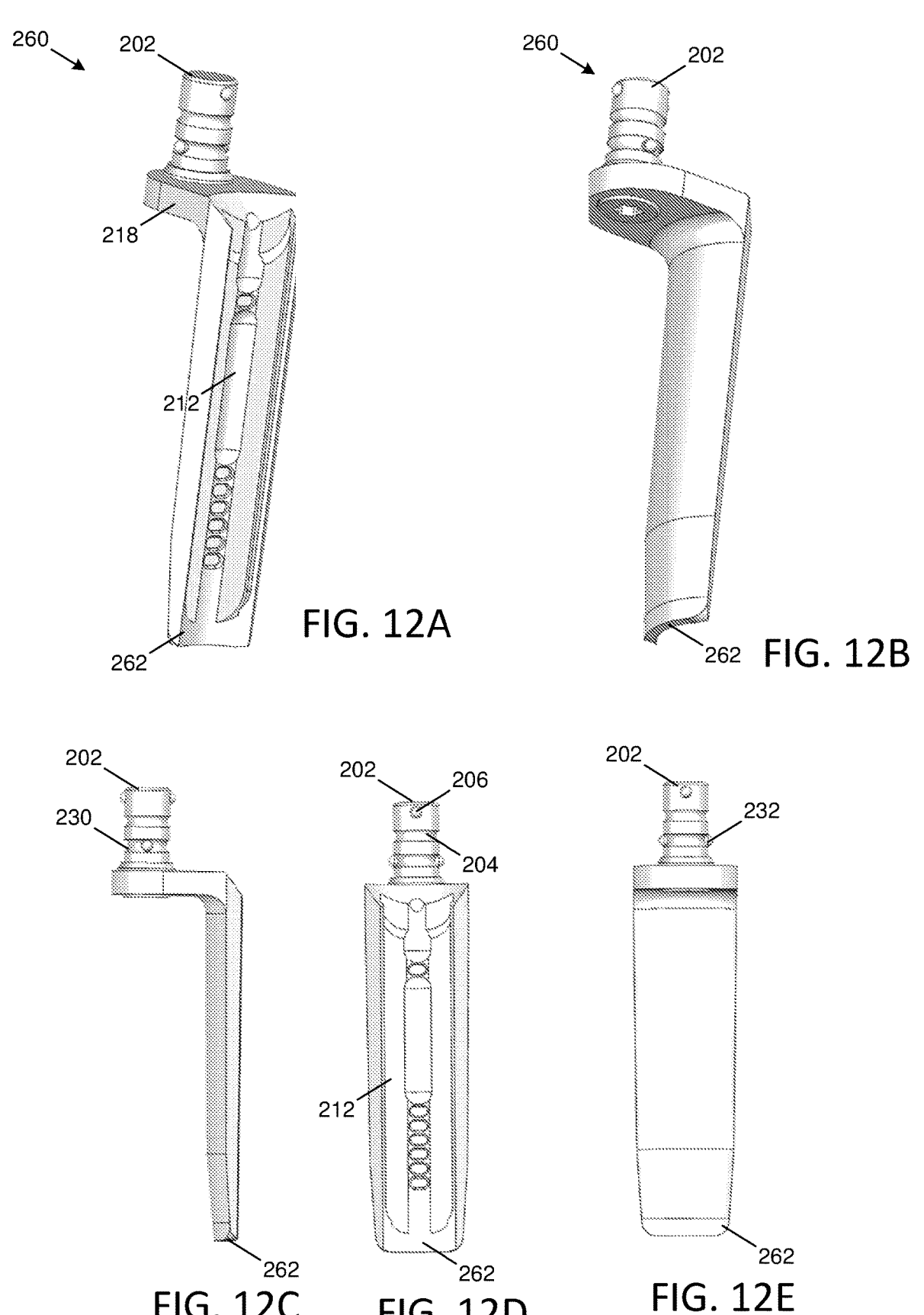
FIGS. 12A-E illustrate a two perspective, back, side and front views of a channel retractor blade.
Figure 13A:
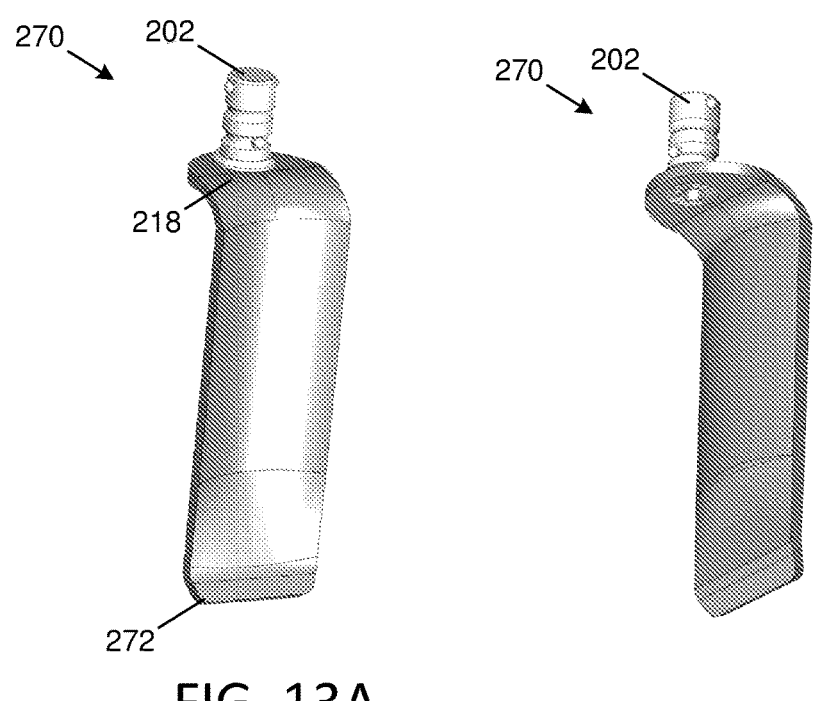
FIGS. 13A-E illustrate a two perspective, back, side and front views of a reverse angle retractor blade.
Figure 13B:
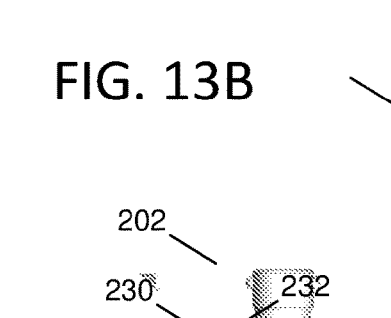
Figures 13C, 13D, 13E:
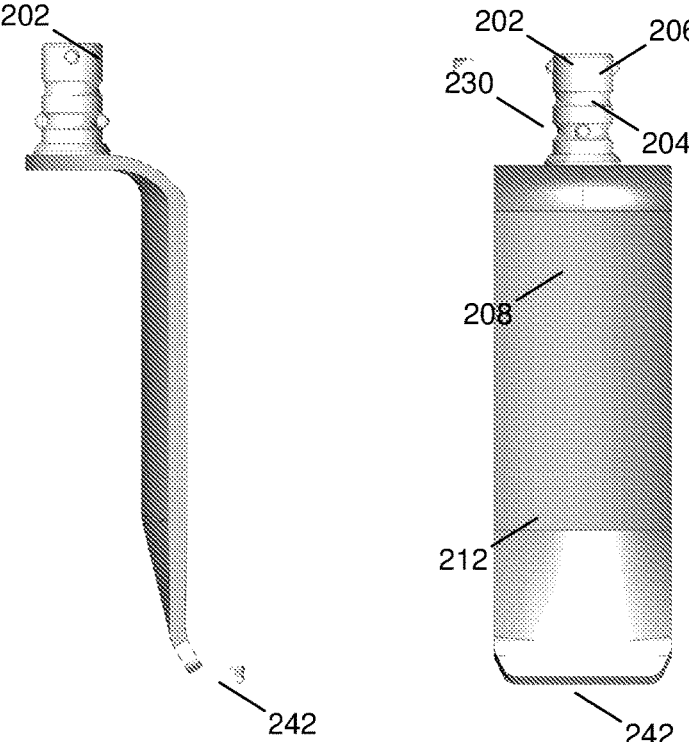

FIG. 8 illustrates an Supine ATP access system 600 where the first ring half 504 is shown in various angular positions relative to the second ring half 506. FIG. 8 illustrates the Supine ATP access system 600 independent of the patient in order to provide a clearer view of the system. The specific number of clamps 104, arms 106, and blades 110 may be more or fewer than the four shown in the Figures. Further, the ring 102 may be a partial or semicircular ring as described in the prior figures. Further, note that FIG. 8 only shows the first ring half 504 being articulated upward, but it may also be articulated downward as well and this is the typical articulation that will be used in the Supine access approach.

The ring components as a whole or individually may be made of a radio-lucent or semi-radio-lucent material composition containing an aluminum alloy and nickel plating to ensure stability and durability. Other radio-lucent materials may be used as well. Further, the ability to adjust the angle of the ring portions allows the ring to be positioned to avoid the field of view of imaging equipment used during a surgical procedure.

FIGS. 9A-9E illustrate two perspective views, as side view, a front view, and a back view, respectively, of a cannulated retractor blade 200. The cannulated retractor blade 200 includes a blade stem 202 attached to a base 218. The blade stem 202 includes a first circular groove 204 and a second circular groove 230. The first circular grove 204 allows the cannulated retractor blade 200 to rotate freely in the arm head 302 (see FIG. 19). The second circular groove 230 allows the cannulated retractor blade 200 to be fixed at a specific angle. This feature will be further described below when the arm 106 is further described below. The blade stem 202 also includes a first cross-pin 206 and a second cross-pin 232 that helps to fix the blade 200 at a fixed angle as will be described later.

The cannulated retractor blade 200 also includes two fixation channels 210 on either edge of a body of the cannulated retractor blade 200. A fixation screw 216 or any other fixation device may be inserted into the fixation channel 210 that is driven into the bone and thereby fixes the position of the blade relative to the bone. The blade may also include only one fixation channel 210.

The cannulated retractor blade 200 further includes a channel 208. The channel 208 has a first end opening in the base 218 and a second end opening at an inner surface of the cannulated retractor blade 200. Numerous devices compatible with this channel including, for example, a light cable or a suction device may be introduced into this channel to provide illumination of the surgical corridor or suction in the surgical corridor. The light source may be a fiber optic light, LED, or any other light source that may be inserted into the channel 208. The angle and location of the channel 208 may be selected so that the light source shines on the target location of the surgical corridor.

The cannulated retractor blade 200 may also include a utility channel 212. The utility channel 212 allows for a sliding element or other device to slide in the utility channel 212 towards the surgical site. A sliding element may be a device configured to fit into and slide along the utility channel 212. Further, the sliding element may be configured to lock in a desired position along the utility channel 212. Such sliding elements or other devices may include screws or implants for delivery to the surgical site, a sliding element for distracting screws or other devices from the surgical site, cameras, lights, sliding element for dynamic retraction where if the anatomy moves during surgical manipulation the blade will not lose its position, suction etc.

The cannulated retractor blade 200 further has a curved distal end 214. The curved distal end 214 may curve outwards towards the patient tissue as illustrated in FIGS. 9A-9E. The distal end 214 of the cannulated blade 200 may curve away from the surgical corridor to form a hook or lip like interface between the back of the blade and the tissues of the patient being retracted. Further, the blade 200 may have a generally curved or convex body.

FIGS. 10A-E illustrate a two perspective, back, side and front views of a reverse tip blade retractor blade 240. The reverse tip blade 240 is similar to the cannulated blade 200 of FIGS. 9A-E, but lacks the channels and the curved distal end 242 curves inward towards the surgical corridor instead as illustrated in FIGS. 10A-E. The curved distal end 242 may be tapered to form a rounded tip that is curved towards the surgical corridor. This distal end retractor blade design enables its stable positioning onto the anterolateral aspect of the vertebral and protection of critical vascular structures. The reverse tip blade 240 has a stem 202 and utility channel 212 that is similar to the stem and utility channel in the cannulated blade 200 of FIGS. 10A-E.

FIGS. 11A-E illustrate a two perspective, back, side and front views of a flat retractor blade 250. The flat blade 250 has a similar stem as the cannulated blade 200 of FIGS. 9A-E, but lacks the fixation channels and utility channel and the flat end 252 extends along surgical corridor and allows for the retraction of the intraabdominal packet. The flat blade 240 has a stem 202 that is similar to the stem in the cannulated blade 200 of FIGS. 10A-E.

FIGS. 12A-E illustrate a two perspective, back, side and front views of a channel retractor blade 260. The channel blade 240 is similar to the cannulated blade 200 of FIGS. 9A-E, but lacks the cannulation, and the curved flat end 262 has a concave curve inward towards the surgical corridor and has a flat distal end allowing a working corridor protecting adjacent vascular structures in the Supine ATP surgical approach when deployed cranially and caudally. The channel blade 260 has a stem 202 and utility channel 212 that is similar to the stem and utility channel in the cannulated blade 200 of FIGS. 10A-E through which a screw shim or fiber optic shim or sliding device can be deployed along the utility channel and fixated onto a bony structure to protect adjacent vascular structures.

FIGS. 13A-E illustrate a two perspective, back, side and front views of a retractor blade 270. The retractor blade 240 has a stem that is similar to the cannulated blade 200 of FIGS. 9A-E. The distal end 272 may be flat and extends away from the surgical corridor. This retractor blade design enables expansion of the operative field of the lateral aspect of the spine by anchoring to the lateral aspect of the spine maintaining exposure of the oblique corridor and intervertebral disc and retracting the psoas muscle and adjacent neurological structures out of the operative field. The retractor blade 240 has a stem 202 that is similar to the stem and utility channel in the cannulated blade 200 of FIGS. 10A-E.

Figure 14:
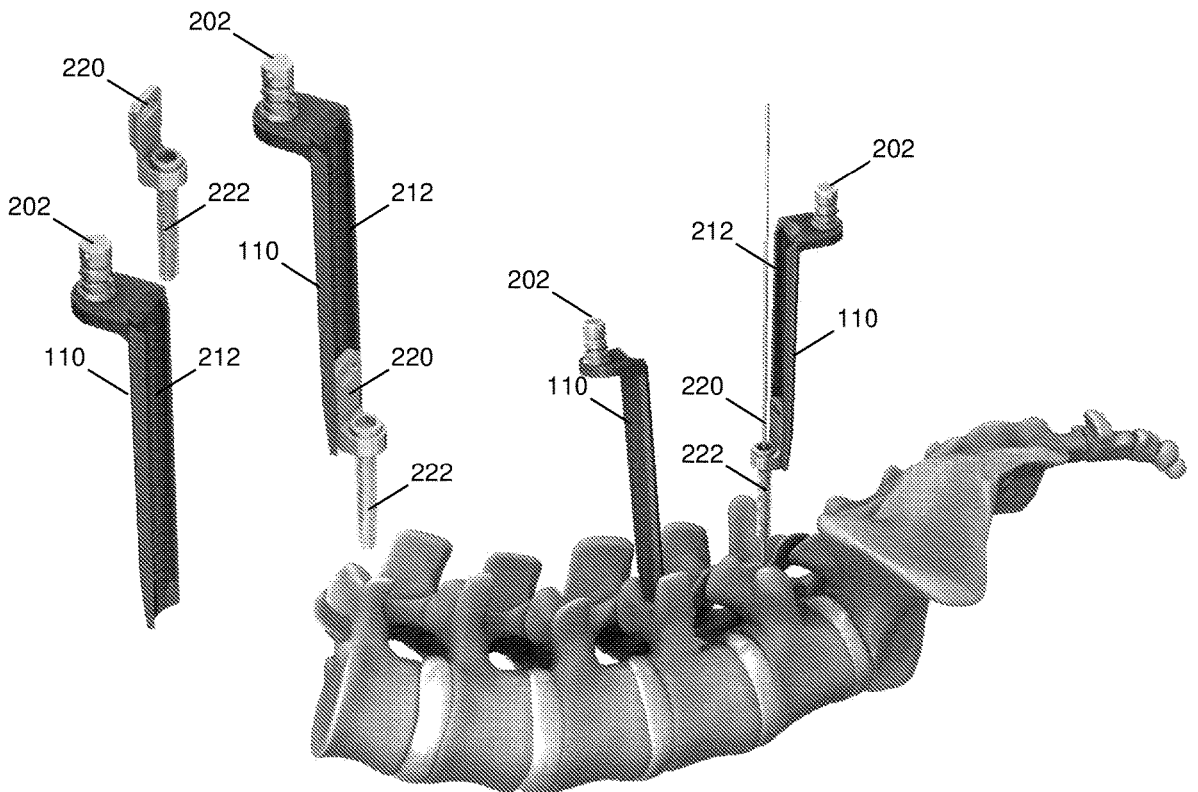
FIG. 14 illustrates as sliding element 220 that includes a screw or other fastener to be placed in the spine or a bony structure.
Figure 15:
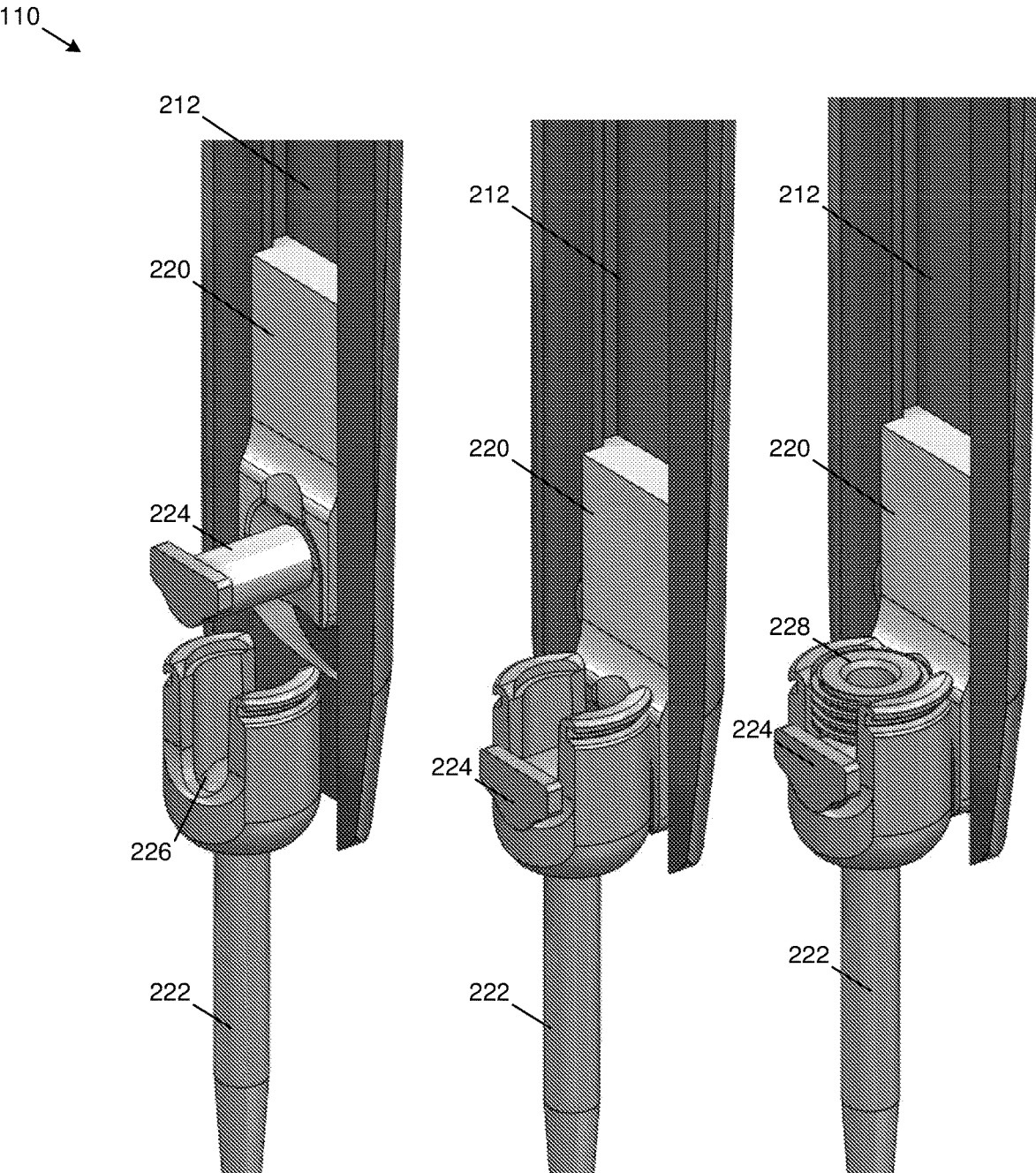
FIG. 15 illustrates the use of a sliding element in the deployment of a fixation screw.
Figure 16:
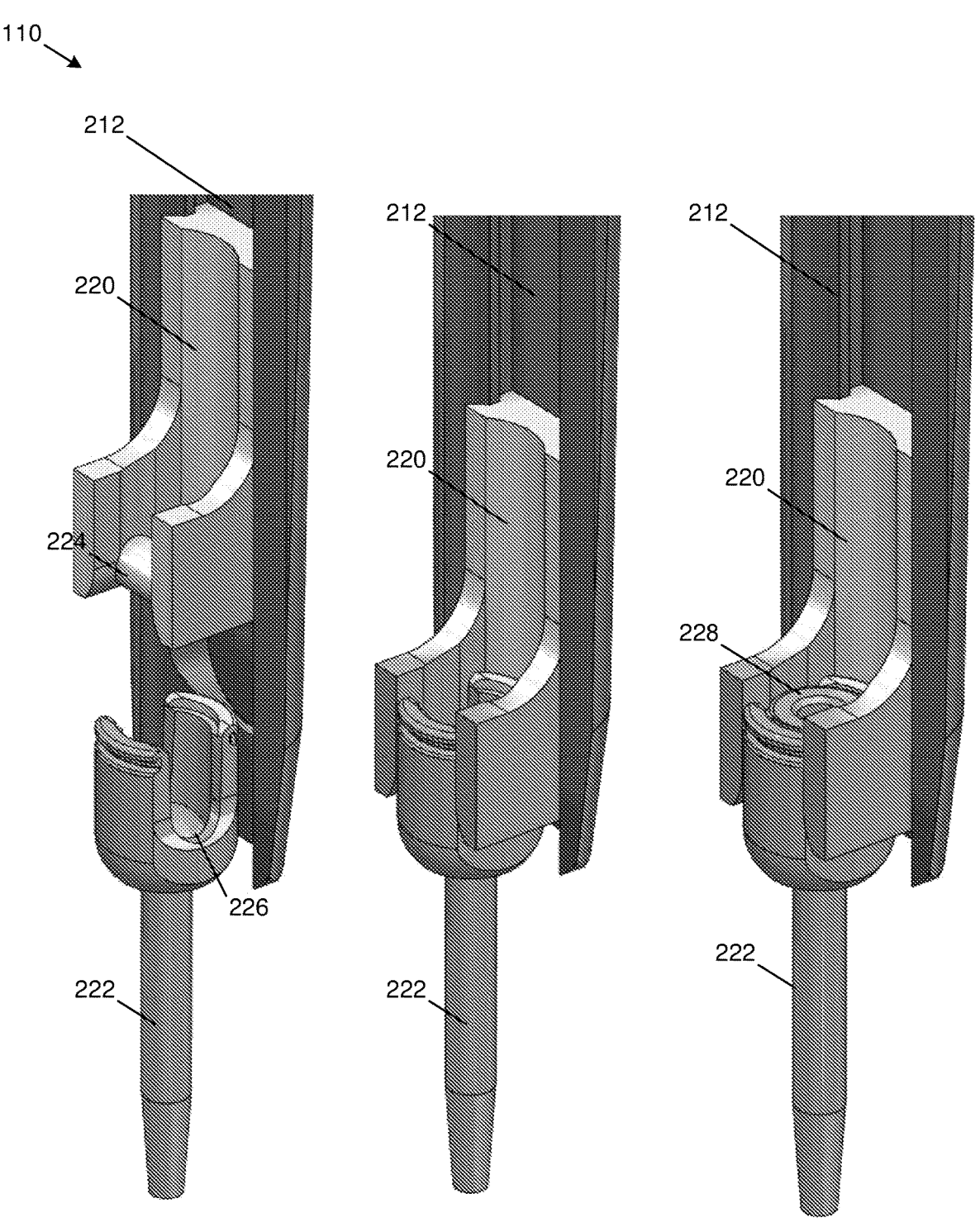
FIG. 16 illustrates the use of a different sliding element for distracting a screw.

FIGS. 14-16 illustrate blades with different sliding elements being used in the utility channel 212. FIG. 14 illustrates as sliding element 220 that includes a screw 222 or other fastener to be placed in the spine or a bony structure. The screw 222 is held by the sliding element 220. The sliding element 220 is then slid into the utility channel 212 and may then be slid down towards the spine or targeted bony structure where the screw 222 may be screwed. Such a configuration may be used to fix the blade 110 to the spine or bony structure. In other embodiments, the sliding element 220 may be designed with a releasable feature so that the sliding element 220 may release the screw 222 once the screw 222 has been attached to the spine or a bony structure. This feature allows for the delivery of screws in a controlled manner to the surgical site. In other embodiments, other types of implants may be attached to the sliding element 220 that allows of controlled and precise delivery of the implant to the surgical site.

FIG. 15 illustrates the use of a sliding element 220 in the deployment of a fixation screw 222. The screw 222 may have a screw slot 226. The sliding element 220 may have a sliding element post 224. The sliding element post 224 extends outward from the sliding element 220. The sliding element post 224 is configured to slid into the screw slot 226 as shown in the middle figure. Then a cap 228 may be screwed into the screw head such that the screw 222 is secured to the sliding element 220. Then the screw 222 may be distracted using the sliding element 220 in a controlled and precise manner.

FIG. 16 illustrates the use of a different sliding element 220 for distracting a screw 222. The screw 222 may have a screw slot 226. The sliding element 220 may have a sliding element post 224. The sliding element post 224 may extend between two extensions from the sliding element. The sliding element post 224 is configured to slid into the screw slot 226 as shown in the middle figure. Then a cap 228 may be screwed into the screw head such that the screw 222 is secured to the sliding element 220. Then the screw 222 may be distracted using the sliding element 220 in a controlled and precise manner.

As discussed above other devices such as light sources, cameras, and a suction line may be placed in the surgical corridor using the utility channel 212. These other devices may include screws or other mechanical structures that allow them to be fixed at specific location along the utility channel 212.

Figure 18A:
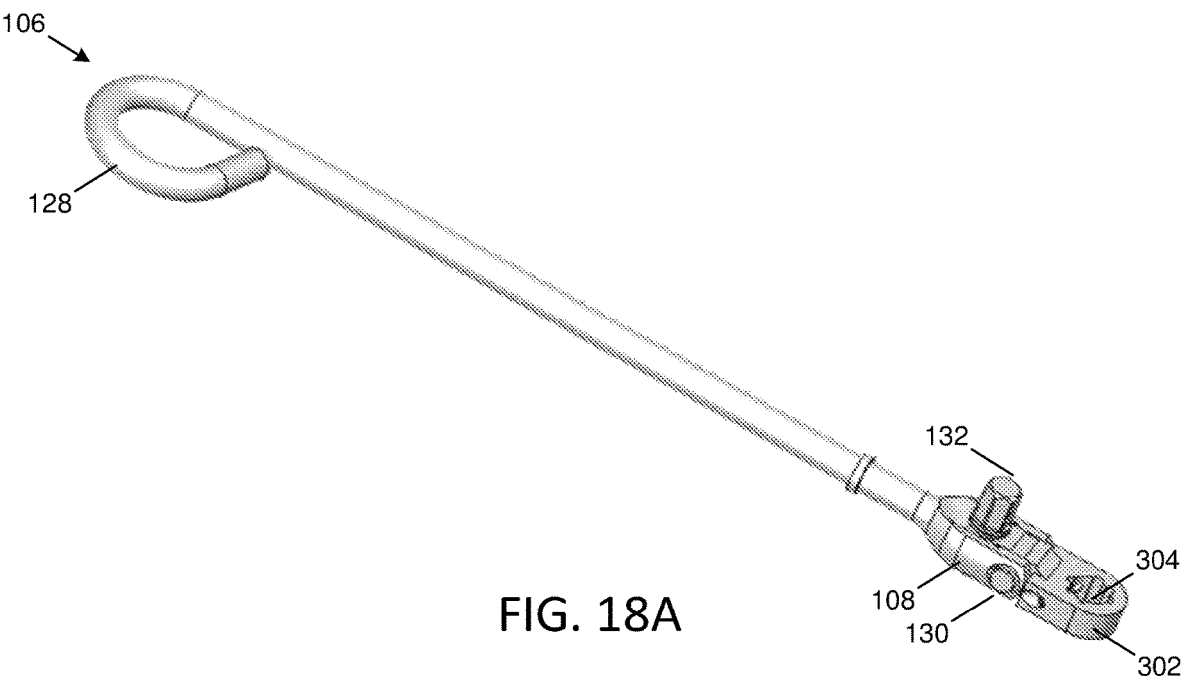
Figure 17:
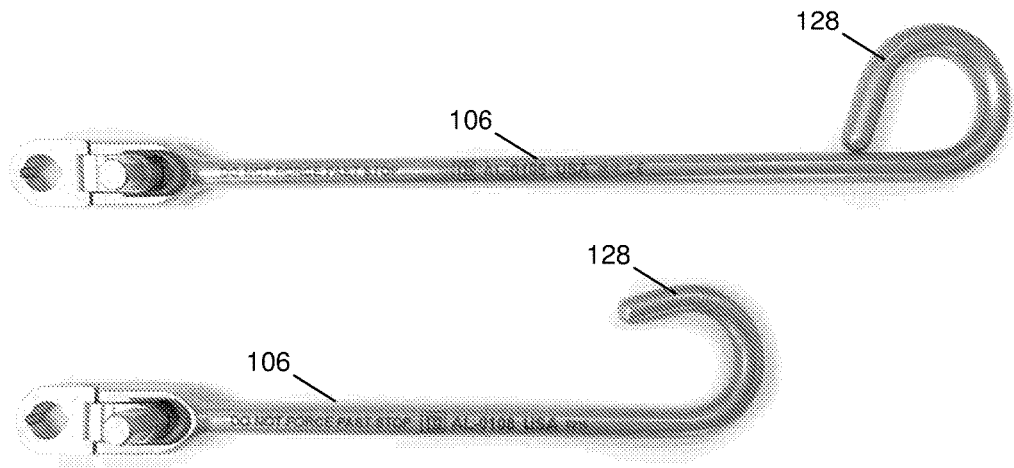

FIGS. 17 and 18A-C illustrate various embodiments of arms 106. FIG. 17 illustrates two arm 106 embodiments. For example, the arms may have hook or loop arm handles 128 as illustrated. Further, a hex fixation bolt may be used to secure the head at a specific angle. A knob shaped fixation bolt may be used to adjust the angle of the hear. FIGS. 18A-C illustrates a perspective view, top view, and side view of the arm 106. The arm may have an arm handle 128 at the proximal end of the arm 106. In this embodiment, the arm handle is a loop but may also be a hook as shown in FIG. 17. The arm 106 includes an arm connector 108 that is configured to connect the arm 106 to a blade 110. The arm connector includes a head 302. The arm connector 108 includes an arm connector pin 130 that allows the head 302 to rotate relative to the rest of the arm 106. This allows for the positioning of the blade at different angles. The arm connector 108 also includes a fixation bolt 132 that fixes the position of the head 302 and prevents further rotation of the head 302 with an engaged retractor blade. The fixation bolt 132 is shown with a hexagonal shape, but the fixation bolt 132 may include a knob that may be used adjust the angle of the head 302 as described above.

FIG. 19 illustrates a close up view of the head 302. The stem opening is shown as having pin slots 306. There are a total of six pin slots 306 shown arranged in pairs opposite one another around the stem opening 304. The pin slots 306 extend along the stem opening 304 from the upper to lower surface of the head 302. The head 302 also includes a detent ball 308 that is biased towards the stem opening 304. The pin slots may correspond to 0°, 45°, and 90° orientation angles for the blades.

The stem 202 of the blade 110 may be placed in the stem opening 304 until the detent ball 308 engages the first circular groove 204. The first cross-pin 206 passes completely through the stem opening 304 via one pair of the pin slots 306. With the blade in this position, the blade is able to freely rotate about the stem. The stem 202 may then be pushed further into the stem opening 304 until the detent ball engages the second circular groove 230. At the same time, the second cross-pin 232 is aligned with one pair of the pin slots 306. The user of the system selects the set of pin slots 306 that will fix the blade 110 in a desired locked position. While six pin slots 306 are shown, more or fewer may be present to allow for other potential locked positions for the blade 110.

This locking feature is similar to the locking feature disclosed in U.S. Pat. No. 9,848,862 to Bass et al. ('862 patent), which is hereby incorporated for all purposes as if fully incorporated herein. The arm 110 described above is an advancement over the arm of the '862 patent in that more than one lock position is possible.

Figure 20:
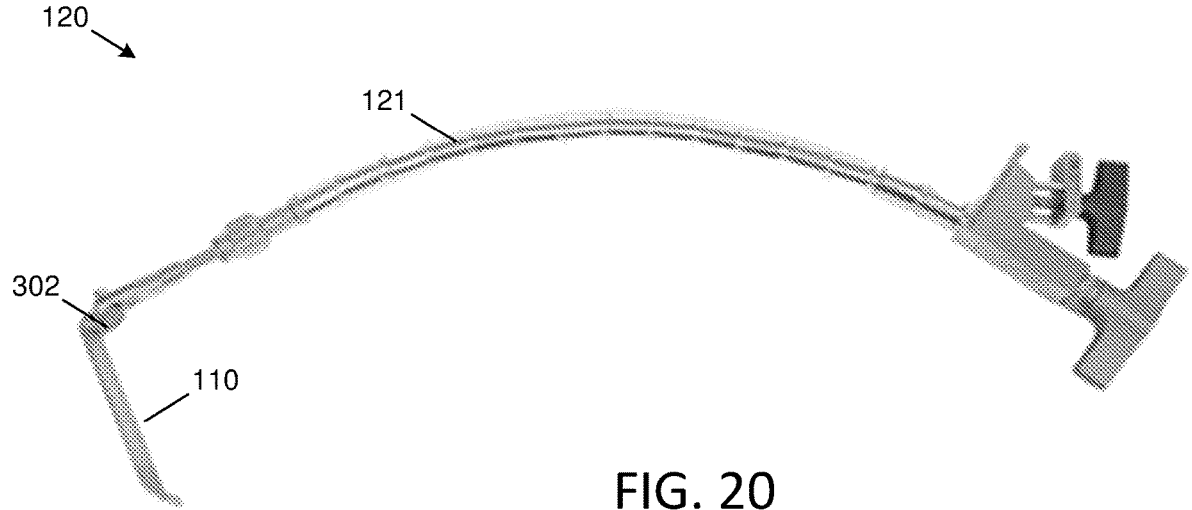
FIG. 20 illustrates an embodiment of a flexible accessory arm.

FIG. 20 illustrates an embodiment of a flexible accessory arm 120. The flexible accessory arm 120 includes a flexible body. The flexible accessory arm 120 also includes two handles that change the shape of the flexible body 121 and fixes the shape in place. Further, the flexible accessory arm 120 may include a head 302 like that described above that accepts a blade 110.

A Supine ATP spinal access method will now be described. Various factors impact the selection of patient for spine fusion procedure-prior abdominal surgery history, prior spine surgery history, history of peripheral artery disease (PAD) and treatment, review spine imaging studies and consideration for the upper lumbar levels. The Supine ATP spinal access method includes the following steps:

The patient is positioned on the operating room table supine with arms abducted 90°.

On the right side of patient, deploy two Positioners: one under the right arm and another just above the right knee.

A surgical belt and two separate wrapping around patient are deployed. The wrapping my include three-inch cloth tape: one at the chest/upper abdomen level and one at the lower extremity level.

A pulse oximeter is placed on the left lower extremity of the patient to monitor the perfusion of the left lower extremity.

A test rotation of the surgical table to approximately 25 degrees left side up is carried out to confirm the safety of the patient.

Patient position starts in the supine position with no table rotation.

Determine the location of the incision by placing a radio-opaque instrument or K-wire on the lateral aspect of the abdominal cavity and performing a direct lateral fluoroscopic image to identify the appropriate in-line trajectory to the targeted lumbar disc space. Once targeted level is identified, and marking is placed on the abdominal wall at the anterior axillary line.

The patient is then draped and prepared using standard sterile technique.

The Supine ATP ring is configured with hinges-one hinge cranially at the 12:00 o'clock position of the ring and the other hinge caudally at the 6:00 o'clock. The hinge is angled at approximately 20-30 degrees along the left side of the patient and parallel to patient on its right side. This parallel and angled ring configuration ensures that imaging is not compromised in the direct anterior-posterior (AP) and direct lateral views.

An approach surgeon initially stands on the right side of the patient, with the patient rotated left side up approximately 25 degrees. The patient may be rotated in the range of 20° to 30°, with the angle being selected to provide a substantially vertical corridor to the spine between the psoas and the arteries. Utilizing a muscle splitting/muscle sparing technique, all three layers of the oblique muscles: External, Internal, and Transverse muscle layers are traversed using two Army-Navy retractors.

Using finger dissection and a sponge stick, the *transversalis* fascia is opened and the retroperitoneal space is developed. A critical step at this stage of the surgical procedure is the identification of the left Psoas muscle.

Once the Psoas muscle is identified, a 25 mm flat end blade 250 on a Hand-Held Blade Arm is deployed and attached at the 9:00 o'clock position of the ring on the right side of the patient. The length of the blade is determined such that once placed at the upper aspect of the Psoas muscle, the blade arm is directly horizontal and inline to the right side of the retractor ring. No further dissection is necessary at this point. The primary objective of this stage of the surgical exposure is the development of the retroperitoneal space corridor and the identification of the Psoas muscle. Special care must be used not to injure the Genitofemoral Nerve which lies directly on top of the Psoas Muscle.

Approach surgeon now moves to the left side of the patient with the patient remaining in the left side up rotation at approximately 25° (but the rotation may be between 20° and 30°.

Two 15 mm channeled blades (e.g., 200, 240, or 260) are then deployed at the 12:00 and 6:00 o'clock retractor ring positions. The determination of the length of the blades is made such that the standard blade arm can attach to ring holder at approximately 90°.

The next steps will depend on the lumbar spine level(s) under surgical exposure. The upper levels of L2-3 and L3-4 require a distinctly different approach than the lower levels of L4-5 and L5-S1 due to vascular anatomical considerations.

Exposure for L2-3 and L3-4 will include the following steps:

Typically, minimal vascular structure release and rotation is needed for these levels.

The 25 mm Straight Blade attached to the hand-held blade handle is then moved over the anterior (ventral) aspect of the lumbar spine in a careful and controlled manner.

The two 15 mm blades are then adjusted medially towards midline of the spine to develop a safe working corridor protecting adjacent critical structures. Screw sliding elements are then deployed along the body of each 15 mm blade to structurally attach them to the respective vertebral body along the spinal column. Careful placement and bony attachment of the sliding elements should be used to avoid injury to any adjacent vascular structures.

Segmental (lumbar) vessels may be encountered at this stage of the surgical exposure. These vessels should be surgical ligated and clipped followed by transection. The vein can often be electrocauterized with bipolar cautery and transected.

Detach the lateral-anterior aspect of the insertion point of the Psoas muscle on the anterior aspect of the spine by carefully protecting the sympathetic nerve and trunk.

Deploy and engage the 25 mm reverse blade attached to a standard blade holder to the lateral aspect of the spine retracting the left Psoas muscle from the surgical corridor. This reverse tip blade is attached at the 3:00 o'clock ring position or the left side of the ring.

Exposure for L4-5 and L5-S1 will include the following steps:

The lower lumbar surgical approach typically requires additional vascular structure release and rotation.

Identification of the left iliac artery and vein and its associated branches is crucial to the defining a safe working corridor to the lumbar column.

Once these vascular structure and branches have been identified and addressed through surgical ligation and clipping followed by transection, depending on the level exposed, the left iliac artery and vein will be rotated towards the right (L4-5 level) and towards the left (L5-S1 level) respectively.

The 25 mm straight blade attached to the hand-held blade handle is then moved over the superior aspect of the lumbar spine in a careful and controlled manner.

The two 15 mm blades are then adjusted medially towards midline of the spine to develop a safe working corridor protecting adjacent critical structures. Screw sliding elements are then deployed along the body of each blade to structurally attach them to the respective vertebral body along the spinal column. Careful placement and bony attachment of the sliding elements should be used to avoid injury to any adjacent vascular structures.

Detach the lateral-anterior aspect of the insertion point of the Psoas muscle on the anterior aspect of the spine by carefully protecting the sympathetic nerve and trunk.

Deploy and engage the 25 mm reverse tip blade attached to a standard blade holder to the lateral aspect of the spine retracting the left Psoas muscle from the surgical corridor. This reverse tip blade is attached at the 3:00 o'clock ring position or the left side of the ring.

The final exposure for all levels will include the following steps:

Once all the Retractor Blades are in place, position a spinal needle on the anterior surface at the midline of the targeted lumbar level.

The patient is then rotated back to neutral supine position and fluoroscopic images, both anterior-lateral (AP) and direct lateral, are used to confirm the midline of the spine and the correct targeted disc spinal level(s).

The fluoroscopy C-arm can be kept in the lateral position to assist the spine surgeon in the disc preparation.

The spine surgeon will perform the disc preparation on the left side of the patient. The patient will remain in the neutral supine position during the rest of the operation facilitating anatomical access and landmark recognition through disc preparation and implant deployment stage of operation.

All imaging is performed in direct AP and lateral image projection-similar to other spine surgery approaches including the anterior lumbar commonly performed.

At the completion of the spinal interbody device placement the following steps are completed: Confirm pulse oximeter is 100%;

Foley catheter is free of blood;

Remove the Shim-screws from the 15 mm blades if used;

Remove the Straight 25 mm blade (right side) confirming no vascular issues;

Remove the 15 mm blades; and

Remove the Reverse Lip 25 mm blade.

Closure of the oblique muscular facial layer(s), deep layer and skin. The blade lengths identified above are meant to only be an example. Other blade lengths may be used as well, depending upon the patient's specific anatomy.

The Supine ATP approach provides various benefits. It allows for a surgeon the access the spine with the patient at an angle (approximately) 25° that allows for a vertical corridor meaning that gravity will help to keep the various anatomical structures including the intraabdominal packet out of the way of the access corridor. This further is a more comfortable position for the surgeon to navigate the anatomy to the spine and manage emergent airway compromise, myocardial infarction and vascular injury. Further, when the patient is then rolled back to a neutral supine position, then the access corridor is in a more comfortable position for the surgeon to operate on the spine due spatial familiarity and anatomical landmark recognition. Further, the Supine ATP approach enables access of challenging patient anatomy including a hostile abdominal wall or bariatric patient profiles.

The ATP access system 100 disclosed herein provides various benefits. It allows for L2-L5 and L5-S1 approaches. The ATP access system 100 uses a narrow cannulated blade for cephalad fixation against bifurcation and laterally against psoas. It may include a reverse lip blade for anterior use, as well as optional blades for caudal retraction.

The blades disclosed herein are multifunction blades that include (1) cannulation for screw or other compatible device deployment, (2) multi-utility blade channel for the delivery of sliding element-based products (i.e., sliding element-based light cable, camera, or pedicle screw interface, suction), (3) a dedicated port at its proximal side for the deployment of compatible devices including a light cable source. Clinical application is not limited to the anterior of the psoas surgical approach, but also other surgical approaches where the combined use of multiple devices would be desirable (i.e., transforaminal lumbar interbody fusion surgery, cardiothoracic surgery for mitral valve repair, anterior lumbar and lateral lumbar surgery).

The design of the arm head also allows for the deployment and locking of the blade in multiple positions giving the surgeon a broader range of patient surgical site access.

The ATP access system provides one system for all levels of the lumbar spine column which leads to more flexibility and lower investment. The ATP system and compatible accessories include design elements which can be leveraged in other surgical applications. The ATP access system features system components compatible with existing, commercially-available surgical access systems enabling seamless technology upgrades for legacy base product systems-facilitating its user familiarity and learning curve. The ATP access system provides flexible blade selection leading to an optimal fit for patient anatomy. The ATP access system also provides a stable platform for secure retraction without movement Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

The invention claimed is:

1. A method for surgically approaching the spine of a patient for spinal surgery, comprising:

positioning the patient on an operating table in supine position in an approximately horizontal orientation;

rotating the patient about a superior-inferior axis of the patient, so that the patient's left side is higher than the patient's right side;

performing an anterior-to-psoas (ATP) surgical approach to the spine;

placing one or more retractors to create a surgical corridor to the spine;

affixing the one or more retractors to a retractor frame;

rotating the patient back to the approximately horizontal position;

performing a surgical procedure though the surgical corridor; and configuring the retractor frame which is a supine ATP ring with a first hinge arranged at a cranial position and a second hinge arranged at a caudal position wherein the hinges are angled at approximately 20 degrees to 30 degrees.

2. The method of claim 1, comprising securing the patient to the operating table, wherein rotating the patient includes rotating the operating table.

3. The method of claim 1, comprising deploying one or more positioners on the right side of the patient.

4. The method of claim 1, comprising deploying a first positioner under the right arm of the patient and a second positioner just above the right knee.

5. The method of claim 1, comprising determining the location of an incision using imaging to identify an appropriate in-line trajectory to a targeted lumbar disc space.

6. The method of claim 5, comprising marking the abdominal wall at the anterior axillary line based upon the identified in-line trajectory.

7. The method of claim 1, wherein the one or more retractors comprise one or more retractor blades, and wherein at least one of the retractor blades is a flat end blade that is placed adjacent to a psoas muscle.

8. The method of claim 7, wherein the flat end blade is connected to the supine ATP ring at a position between the hinges on the left side of the patient.

9. The method of claim 1, wherein the patient is rotated approximately 20 degrees to 30 degrees.

10. The method of claim 1, wherein a first retractor of the one or more retractors has a first blade, a second retractor of the one or more retractors has a second blade that is placed at an approximal cranial position on the supine ATP ring, and a third retractor of the one of the one or more retractors has a third blade that is placed at an approximal caudal position on the supine ATP ring.

11. The method of claim 10, further comprising securing the second blade and the third blade to a vertebral body.

12. The method of claim 1, wherein each retractor of the one or more retractors comprises a retractor blade wherein the retractor blade is a reverse tip blade that is placed to retract a left psoas muscle from the surgical corridor and attached at a position between the hinges on the right side of the patient.

13. The method of claim 1, comprising performing a disc preparation on the left side of the patient.

14. The method of claim 1, comprising implanting a device in the spine.

15. The method of claim 14, comprising delivering the device to the spine using a sliding element in a channel of a retractor blade of the one or more retractors.

16. The method of claim 1, comprising lighting the surgical corridor using a light source on a sliding element in a channel of a retractor blade of the one or more retractors.

17. The method of claim 1, comprising applying suction to the surgical corridor using a suction device on a sliding element in a channel of a retractor blade of the one or more retractors.

18. The method of claim 1, comprising lighting the surgical corridor using a light source in a channel of a retractor blade of the one or more retractors, wherein the channel extends from the top of a base of the retractor blade to a surface of the retractor blade facing the surgical corridor.

19. The method of claim 1, comprising applying suction to the surgical corridor using a suction device in a channel of a retractor blade of the one or more retractors, wherein the channel extends from the top of a base of the retractor blade to a surface of the retractor blade facing the surgical corridor.

20. The method of claim 1, comprising securing a retractor blade of the one or more retractors to a vertebral body using a fastener inserted through a fastening channel extending along the length of the retractor blade.

21. A method for surgically approaching the spine of a patient for spinal surgery, comprising:

positioning the patient on an operating table in supine position in an approximately horizontal orientation;

rotating the patient about a superior-inferior axis of the patient, so that the patient's left side is higher than the patient's right side;

performing an anterior-to-psoas (ATP) surgical approach to the spine;

placing one or more retractors to create a surgical corridor to the spine;

affixing the one or more retractors to a retractor frame;

rotating the patient back to the approximately horizontal position;

performing a surgical procedure though the surgical corridor;

determining the location of an incision using imaging to identify an appropriate in-line trajectory to a targeted lumbar disc space; and marking the abdominal wall at the anterior axillary line based upon the identified in-line trajectory.

* * * * *